United States Patent [19]

Aristoff

[11] Patent Number: 4,683,330

[45] Date of Patent: Jul. 28, 1987

[54] INTERPHENYLENE CARBACYCLIN DERIVATIVES

[75] Inventor: Paul A. Aristoff, Portage, Mich.

[73] Assignee: The Upjohn Company, Kalamazoo, Mich.

[21] Appl. No.: 690,804

[22] Filed: Jan. 11, 1985

Related U.S. Application Data

[63] Continuation-in-part of Ser. No. 587,337, Mar. 8, 1984, abandoned.

[51] Int. Cl.$^4$ ............................................. C07C 177/00
[52] U.S. Cl. ...................................... 560/51; 560/117; 560/56; 560/45; 562/444; 562/466; 562/499; 562/453; 564/99; 564/152; 564/158; 564/171; 564/174; 564/374; 564/384; 564/427; 564/453; 564/454; 564/80; 564/88; 564/89; 564/90; 564/92; 564/93; 564/95; 564/97; 564/98; 568/633; 568/808; 568/817; 549/66; 549/78; 549/305; 549/465; 549/496; 549/499; 549/501; 549/502; 549/79; 548/540; 544/155; 544/380; 546/203; 546/204; 546/283; 546/284; 546/285
[58] Field of Search ...................... 568/633, 808, 817; 544/115, 380; 546/203, 204, 283, 284, 255; 542/429; 549/78, 79, 66, 65; 260/347.3, 347.4, 347.8, 464, 465 D, 239 BC, 326.4, 326.36, 326.35; 560/51, 56, 45, 117; 562/499, 453, 466, 444; 564/374, 384, 427, 453, 454, 177, 178, 152, 158, 80, 88, 89, 92, 95, 98, 93, 99, 97

[56] References Cited

U.S. PATENT DOCUMENTS

| | | | |
|---|---|---|---|
| 4,180,657 | 12/1979 | Sih ........................................ | 542/426 |
| 4,192,891 | 3/1980 | Haslanger ............................ | 424/305 |
| 4,225,508 | 9/1980 | Sih .................................... | 260/346.22 |
| 4,238,414 | 12/1980 | Morton ................................ | 564/453 |
| 4,306,075 | 12/1981 | Aristoff ................................ | 560/56 |
| 4,306,076 | 12/1981 | Nelson ................................ | 560/56 |
| 4,349,689 | 9/1982 | Aristoff ............................. | 560/117 |

FOREIGN PATENT DOCUMENTS

| | | |
|---|---|---|
| 0024943 | 11/1981 | European Pat. Off. . |
| 0087237 | 8/1983 | European Pat. Off. . |
| 2900352 | 7/1979 | Fed. Rep. of Germany . |
| 4063059 | 5/1979 | Japan . |
| 4063060 | 5/1979 | Japan . |
| 4024865 | 5/1979 | Japan . |
| 2012265 | 7/1979 | United Kingdom . |
| 2013661 | 8/1979 | United Kingdom . |
| 2017699 | 10/1979 | United Kingdom . |
| 2070596 | 9/1981 | United Kingdom . |

OTHER PUBLICATIONS

Aristoff, P. A., et al., Advances in Prostaglandin, Thromboxane, and Leukotriene Research, 11, 1983, pp. 267-274, "Synthesis and Structure-Activity Relationship of Novel Stable Prostacylin Analogs".
Aristoff, P. A. and Harrison, A. W., Tetrahedron Letters 23 (No. 20), 1982; pp. 2067-2070, "Synthesis of Benzindene Prostaglandins: A Novel Potent Class of Stable Prostacyclin Analogs".
Aristoff, P. A., J. Org. Chem., 46 (No. 9), 1981, pp. 1954-1957, "Practical Synthesis of 6a-Carbaprostaglandin $I_2$".
Barco, A., et al., J. Org. Chem. 45 (No. 32), 1980, pp. 4776-4778, "A New Elegant Route to a Key Intermediate for the Synthesis of 9(O)-Methanoprostacyclin".
Konishi, Y., et al., Chem. Lett. 1979, pp. 1437-1440, "A Synthesis of 9(O)-Methanoprostacyclin".
Kojima, K. and Sakai, K., Tetrahedron Letters 39, 1978, pp. 3743-3746, "Total Synthesis of 9(O)-Methanoprostacyclin and Its Isomers".
Morton, D. R., Jr. and Brokaw, F. C., J. Org. Chem. 44 (No. 16), 1979, pp. 2880-2887, "Total Synthesis of 6a--Carbaprostaglandin $I_2$ and Related Isomers".
Nicolaou, K. C. et al., J.C.S. Chem. Comm. 1978, pp. 1067-1068, "Total Synthesis of Carboprostacyclin, A Stable and Biologically Active Analogue of Prostacyclin ($PGI_2$)".
Shibasaki, M., et al., Chem. Lett. 1979, pp. 1299-1300, "A Stereo and Regiospecific Route to the Synthetic Intermediate for the Synthesis of 9(O)-Methanoprostacyclin".
Shibasaki, M., et al., Tetrahedron Letters, 5, 1979, pp. 433-436, "New Synthetic Routes to 9(O)-Methanoprostacyclin, A Highly Stable and Biologically Potent Analog of Prostacyclin".
Skuballa, V. W. and Vorgruggen, H., Angew. Chem. 93, (No. 12), 1981, pp. 1080-1081, "Ein Neuer Weg Zu 6a-Carbacyclinen-Synthese Eines Stabilen, Biologisch Potenten Prostacyclin-Analogons".
Sugie, A., et al., Tetrahedron Letters, 28, 1979, pp. 2607-2610, "Stereocontrolled Approaches to 9(O)-Methanoprostacyclin".
Yamazaki, M., et al., Chem. Lett. 1981, pp. 1245-1248, "1,2-Carbonyl Transposition of Cis-Bicyclo[3.3.0]Octan-2-One to Its 3-One Skeleton: Appl. to Syntheses of $d_1$-Hirsutic Acid and $d_1$-9(O)-Methanoprostacyclin".

*Primary Examiner*—Paul J. Killos
*Attorney, Agent, or Firm*—L. Ruth Hattan

[57] ABSTRACT

A compound of the formula and intermediates useful in preparing same.

14 Claims, No Drawings

INTERPHENYLENE CARBACYCLIN DERIVATIVES

CROSS REFERENCE TO RELATED APPLICATION

This application is a continuation-in-part of U.S. application Ser. No. 587,337 filed Mar. 8, 1984, now abandoned.

FIELD OF INVENTION

The present invention relates to novel pharmaceutically useful compounds which are carbacyclin analogs having a tricyclic nucleus.

PRIOR ART

Related interphenylene carbacyclins are described and claimed in U.S. Pat. No. 4,306,075, U.S. Pat. No. 4,306,076, and EP No. 87237 (Derwent No. 754477). Compounds having a 5-membered oxa ring are described in European Pat. No. 24-943 (Derwent No. 19801D).

Carbacyclin and closely related compounds are known in the art. See Japanese Kokai Nos. 63,059 and 63,060, also abstracted respectively as Derwent Farmdoc CPI Nos. 481454B/26 and 48155B/26. See also British published specification No. 2,012,265 and German Offenlungsschrift No. 2,900,352, abstracted as Derwent Farmdoc CPI No. 54825B/30. See also British published application Nos. 2,017,699 and 2,013,661 and U.S. Pat. No. 4,238,414.

The synthesis of carbacyclin and related compounds is also reported in the chemical literature, as follows: Morton, D. R., et al, J. Org. Chem., 44: 2880-2887 (1979); Shibaski, M., et al, Tetrahedron Lett., 433-436 (1979); Kojima, K., et al, Tetrahedron Lett., 3743-3746 (1978); Nicolaou, K. C., et al, J. Chem. Soc., Chemical Communications, 1067-1068 (1978); Sugie, A., et al, Tetrahedron Lett., 2607-2610 (1979); Shibasaki, M., Chem. Lett., 1299-1300 (1979), and Hayashi, M., Chem. Lett., 1437-40 (1979); Aristoff, P. A., J. Org. Chem. 46, 1954-1957 (1981); Yamazaki, M., et al, Chem. Lett., 1245-1248 (1981); and Barco, A., et al, J. Org. Chem. 45, 4776-4778 (1980); and Skuballa, W., et al, Angew. Chem. 93, 1080-1081 (1981). The utility and synthesis of compounds closely related to those claimed herein is described in Aristoff, P. A., and Harrison, A. W., Tetrahedron Lett. 23, 2067-2070 (1982) and in Advances in Prostaglandin, Thromboxane, and Leukotriene Research, Vol 11, 267 (1983).

7-Oxo and 7-hydroxy-CBA$_2$ compounds are apparently disclosed in U.S. Pat. No. 4,192,891. 19-Hydroxy-CBA$_2$ compounds are disclosed in U.S. Pat. No. 4,225,508. CBA$_2$ aromatic esters are disclosed in U.S. Pat. No. 4,180,657. 11-Deoxy-$\Delta^{10}$- or $\Delta^{11}$-CBA$_2$ compounds are described in Japanese Kokai No. 77/24,865, published 24 February 1979.

SUMMARY OF THE INVENTION

The present invention provides compounds of Formula I wherein:
Q is
(1) —COOR$_1$, wherein R$_1$ is
  (a) hydrogen;
  (b) (C$_1$–C$_{12}$) alkyl;
  (c) (C$_3$–C$_{10}$) cycloalkyl;
  (d) (C$_7$–C$_{12}$) aralkyl;
  (e) phenyl, optionally substituted with one, 2 or 3 chloro or (C$_1$–C$_3$) alkyl;
  (f) phenyl substituted in the para position by
    (i) —NHCOR$_{25}$,
    (ii) —COR$_{26}$,
    (iii)

or
    (iv) —CH=N—NHCONH$_2$ wherein R$_{25}$ is methyl, phenyl, acetamidophenyl, benzamidophenyl, or —NH$_2$; R$_{26}$ is methyl, phenyl, —NH$_2$, or methoxy; R$_{54}$ is phenyl or acetamidophenyl; inclusive; or
  (g) a pharmacologically acceptable cation;
(2) —CH$_2$OH;
(3) —COL$_4$, wherein L$_4$ is
  (a) amino of the formula —NR$_{51}$R$_{52}$ wherein R$_{51}$ and R$_{52}$ are
    (i) hydrogen,
    (ii) (C$_1$–C$_{12}$) alkyl,
    (iii) (C$_3$–C$_{10}$) cycloalkyl,
    (iv) (C$_7$–C$_{12}$) aralkyl,
    (v) phenyl, optionally substituted with one 2 or 3 chloro, (C$_1$–C$_3$) alkyl, hydroxy, carboxy, (C$_2$–C$_5$) alkoxycarbonyl, or nitro,
    (vi) (C$_2$–C$_5$) cyanoalkyl,
    (vii) (C$_2$–C$_5$) carboxyalkyl,
    (viii) (C$_2$–C$_5$) carbamoylalkyl,
    (ix) (C$_3$–C$_6$) acetylalkyl,
    (x) (C$_7$–C$_{11}$) benzoalkyl, optionally substituted by one, 2 or 3 chloro, (C$_1$–C$_3$) alkyl, hydroxy, (C$_1$–C$_3$) alkoxy, carboxy, (C$_2$–C$_5$) alkoxy carbonyl, or nitro,
    (xi) pyridyl, optionally substituted by one, 2 or 3 chloro, (C$_1$–C$_3$) alkyl, or (C$_1$–C$_3$) alkoxy,
    (xii) (C$_6$–C$_9$) pyridylalkyl optionally substituted by one, 2 or 3 chloro, (C$_1$–C$_3$) alkyl, hydroxy, or (C$_1$–C$_3$) alkoxy,
    (xiii) (C$_1$–C$_4$) hydroxyalkyl,
    (xiv) (C$_1$–C$_4$) dihydroxyalkyl,
    (xv) (C$_1$–C$_4$) trihydroxyalkyl, with the proviso that not more than one of R$_{51}$ and R$_{52}$ is other than hydrogen or alkyl;
  (b) cycloamino selected from the group consisting of pyrrolidino, piperidino, morpholino, piperazino, hexamethylenimino, pyrrolino, or 3,4-didehydropiperidinyl optionally substituted by one or 2 (C$_1$–C$_{12}$) alkyl of one to 12 carbon atoms, inclusive;
  (c) carbonylamino of the formula —NR$_{53}$COR$_{51}$ wherein R$_{53}$ is hydrogen or (C$_1$–C$_4$) alkyl and R$_{51}$ is other than hydrogen, but otherwise defined as above;
  (d) sulfonylamino of the formula —NR$_{53}$SO$_2$R$_{51}$, wherein R$_{51}$ and R$_{53}$ are defined in (c);
(4) —CH$_2$NL$_2$L$_3$ wherein L$_2$ and L$_3$ are hydrogen or (C$_1$–C$_4$) alkyl, being the same or different, or the pharmacologically acceptable acid addition salts thereof when X$_1$ is —CH$_2$NL$_2$L$_3$;
(5) —CN;
wherein Z$_4$ is —CH$_2$—, —CH$_2$CH$_2$—, —CF$_2$— or —CH$_2$CF$_2$;
wherein L$_{20}$ is α-OH,β-H; α-H,β-OH; H,H; α-CH$_3$,β-H; α-CH$_2$OH,β-H; =O; or =CH$_2$; wherein L$_{60}$ is hydrogen or $L_{20}$ and $L_{60}$ taken together form a double bond between positions 10 and 11;

wherein $Y_1$ is $-CH_2CH_2-$, $-SCH_2-$, $-C\equiv C-$, trans-$CH=CH-$, or cis-$CH=CH-$;

wherein

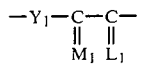

taken together is $$-CH=NNH\overset{O}{\underset{\|}{C}}-NH-;$$

wherein $M_1$ is $\alpha$-H:$\beta$-H; =O; $\alpha$-OH:$\beta$-$R_5$; or $\alpha$-$R_5$:$\beta$-OH; wherein $R_5$ is hydrogen or methyl;

wherein $L_1$ is (1) $\alpha$-$R_3$:$\beta$-$R_4$, $\alpha$-$R_4$:$\beta$-$R_3$, or mixtures thereof wherein $R_3$ and $R_4$ are hydrogen, methyl, or fluoro, being the same or different, with the proviso that one of $R_3$ and $R_4$ is fluoro only when the other is hydrogen or fluoro;

(2) or when $M_1$ is $\alpha$-H:$\beta$-H, $L_1$ is $\alpha$-OH:$\beta$-$R_3$, $\alpha$-$R_3$:$\beta$-OH; or a mixture of $\alpha$-OH:$\beta$-$R_3$ and $\alpha$-$R_3$:$\beta$-OH wherein $R_3$ is hydrogen, methyl, vinyl, or ethynyl;

wherein $R_7$ is $-(CH_2)_mOCH_3$, wherein m is an integer from 2 to 5, inclusive and said group is straight or branched; or wherein

taken together is (1)

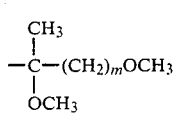

wherein m is an integer of from 2 to 5 inclusive;

(2)

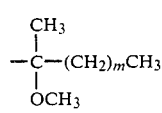

wherein m is an integer of from 2 to 5 inclusive;

(3)

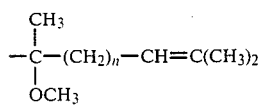

wherein n is an integer of from 1 to 4 inclusive; or (4)

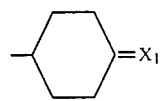

wherein $X_1$ is =O; F,F; $\alpha$-H,$\beta$-OH and $\alpha$-OH,$\beta$-H;

(5)

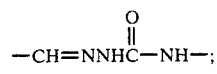

wherein X is $-O-$, $-S-$, or $-NH$;

(6)

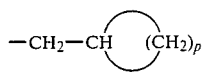

wherein X is as defined above;

(7)

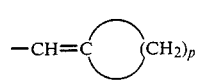

wherein X is as defined above;

wherein $$-\underset{\underset{M_1}{\|}}{\overset{}{C}}-\underset{\underset{L_1}{\|}}{\overset{}{C}}-R_7$$

taken together is (1)

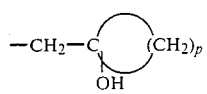

wherein p is an integer of from 3 to 7 inclusive;

(2)

-CH<sub>2</sub>-⌬(CH<sub>2</sub>)<sub>p</sub>-1 wherein p is as defined above;

(3)

-CH<sub>2</sub>-CH⌬(CH<sub>2</sub>)<sub>p</sub> wherein p is as defined above; or (4)

-CH<sub>2</sub>-C(OH)⌬(CH<sub>2</sub>)<sub>p</sub> wherein p is as defined above; and the individual optical enantiomers thereof.

The intermediates depicted in Formulas I(a) to I(d) which are useful in the preparation of compounds of Formula I are also as part of the present invention wherein $R_7$, $L_{20}$ and $L_{60}$ have the same meaning as in Formula I; $Y_2$ is —SCH$_2$— or —CH$_2$CH$_2$—; $M_2$ is H,H; =O; $\alpha$-H,$\beta$-ORx or $\alpha$-ORx,$\beta$-H or mixtures of $\alpha$ and $\beta$-H,ORx wherein Rx is a hydroxy protecting group; $L_2$ is the same as $L_1$ in Formula I only any hydroxy group is protected as ORx wherein Rx is as defined below; $X_2$ is H or CH$_3$; and alkyl has from 1 to 4 carbon atoms.

The compounds of Formula I have useful pharmacological properties as defined below.

DETAILED DESCRIPTION OF INVENTION

In the compounds of the present invention, and as used herein, ('''') denotes the $\alpha$-configuration, (—) denotes the $\beta$-configuration, ($\sim$) denotes $\alpha$- and/or $\beta$-configuration or the E and/or Z isomer.

With regard to the divalent groups described above, i.e., $L_{20}$, $M_1$ and $L_1$ said divalent groups are defined in terms of an $\alpha$-substituent and a $\beta$-substituent which means that the $\alpha$-substituent of the divalent group is in the alpha configuration with respect to the plane of the C-8 to C-12 cyclopentane ring and the $\beta$-substituent is in the beta configuration with respect to said cyclpentane ring.

The carbon atom content of various hydrocarbon containing groups is indicated by a prefix designating the minimum and maximum number of carbon atoms in the moiety. For example, in defining the moiety $L_4$ in the —CO$L_4$ substituent group the definition (C$_1$–C$_{12}$)alkyl means that $L_4$ can be an alkyl group having from one to 12 carbon atoms. Additionally, any moiety so defined includes straight chain or branced chain groups. Thus (C$_1$–C$_{12}$)alkyl as set forth above includes straight or branched chain alkyl groups having from 1 to 12 carbon atoms and as additional illustration, when $L_4$ represents, for example, (C$_2$–C$_5$)carboxylalkyl, the alkyl moiety thereof contains from 1 to 4 carbon atoms and is a straight chain or a branched chain alkyl group. Similarly a C$_3$–C$_5$ alkenyl group as may be present on the cycloalkyl group represented by —C(L$_1$)R$_7$ contains from 3 to 5 carbon atoms and one double bond in the chain.

In Formula I when the hydrogen at position 9 is beta the compounds are named as 9-dexoy-2',9$\alpha$-methano-3-oxa-4,5,6-trinor-3,7-(1',3'-interphenylene)PGF$_1$ compounds, and when it is alpha the compounds are named as 9-deoxy-2',9$\beta$-methano-3-oxa-4,5,6-trinor-3,7-(1',3'-interphenylene)PGF$_1$ compounds.

When $Z_4$ is —CF$_2$— the compounds of Formula I are also characterized as 2,2-difluoro and when $Z_4$ is —CH$_2$CF$_2$— the compounds are characterized as 2$\alpha$-homo-2,2-difluoro.

When $R_5$ is methyl, the carbacyclin analogs are all named as "15-methyl-" compounds. Further, except for compounds wherein $Y_1$ is cis-CH=CH—, compounds wherein the $M_1$ moiety contains an hydroxyl in the beta configuration are additionally named as "15-epi-" compounds.

For the compounds wherein $Y_1$ is cis-CH=CH—, then compounds wherein the $M_1$ moiety contains an hydroxyl in the alpha configuration are named as "15-epi-CBA" compounds. For a description of this convention of nomenclature for identifying C-15 epimers, see U.S. Pat. No. 4,016,184, issued Apr. 5, 1977, particularly columns 24-27 thereof.

The compounds of the present invention which contain —(CH$_2$)$_2$—, cis—CH=CH—, trans—CH=CH— or —C≡C— as the $Y_1$ moiety, are accordingly referred to as "13,14-dihydro", "cis-13", "trans-13", or "13,14-didehydro" compounds, respectively. Compounds wherein $Y_1$ is —SCH$_2$— are named as "13-thio" compounds.

Compounds wherein $M_1$ is H,H are named as "15-deoxy" compounds. Compounds wherein $M_1$ is =O are named as "15-oxo" compounds.

Compounds wherein

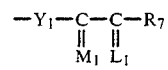

taken together is

are named as 13,14,15,16,17,18,19,20-octanor-12-[N-(R$_7$-carbamoyl)hydrazanomethyl].

When R$_7$ is —(CH$_2$)$_m$—OCH$_3$ the compounds are named as 18-methoxy-19,20-di-nor when m is 2; 20-methoxy-20-nor when m is 3; 20-methoxy when m is 4; and 20-methoxymethyl when m is 5.

When —C(L$_1$)R$_7$ is

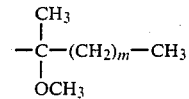

the compounds are named as 16-methyl-16-methoxy-20-nor compounds when m is 2; 16-methyl-16-methoxy when m is 3; 16,20-dimethyl-16-methoxy when m is 4; and 16-methyl-16-methoxy-20-ethyl when m is 5.

When —C(L$_1$)R$_7$ is

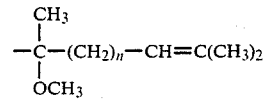

the compounds are named as 16,19-dimethyl-16-methoxy-18,19-dehydro when n is 1; 16-methyl-16-methoxy-19,20-dehydro-20,20-dimethyl when n is 2; when n is 3 the compounds are named as 16-methyl-16-methoxy-20(2-isopropylidene) compounds; and when n is 4 the compounds are named as 16-methyl-16-methoxy-20(1-isobutylidene) compounds.

When —C(L$_1$)R$_7$ is

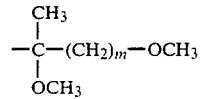

and m is 2 the compounds are named as 16-methyl-16,18-dimethoxy-19,20-nor compounds; when m is 3, as 16-methyl-16,19-dimethoxy-20-nor compounds; when m is 4, as 16-methyl-16,20-dimethoxy compounds; and when m is 5, as 16-methyl-16-methoxy-20-methoxymethyl compounds.

When $C(L_1)R_7$ is definitions (4) through (8) the compounds are named as 17,18,19,20-tetranor-16-substituted compounds with the name of the 16-position substituent being one of the substituted cycloalkyl or heterocyclic groups designated in definitions (4)–(8). When —C(M)—$C(L_1)R_7$ taken together is any of definitions (1) through (4) the compounds are named as 15-deoxy-16,17,18,19,20-pentanor-15-substituted compounds with the 15-position substituent depending on the definition designated in (1) through (6).

When at least one of $R_3$ and $R_4$ is not hydrogen then there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the carbacyclin analogs so represented contain an asymmetric carbon atom at C-16. Accordingly, two epimeric configurations are possible: "(16S)" and "(16R)". Further, there is described by this invention the C-16 epimeric mixture: "(16RS)".

When Q is —CH$_2$OH, the compounds so described are named as "2-decarboxy-2-hydroxymethyl" compounds.

When Q is —CH$_2$NL$_2$L$_3$, the compounds so described are named as "2-decarboxy-2-aminomethyl" or "2-(substituted amino)methyl" compounds.

When Q is —COL$_4$, the novel compounds herein are named as amides. Further, when Q is —COOR$_1$ and R$_1$ is other than hydrogen the novel compounds herein are named as esters and salts.

When Q is CN the novel compounds herein are named as 2-decarboxy-2-cyano compounds.

Examples of phenyl esters substituted in the para position (i.e., Q is —COOR$_1$, R$_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is —COL$_4$) include the following:

(1) Amides within the scope of alkylamino groups of the formula NR$_9$R$_{10}$ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tert-butylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N benzyl-amide. Amide within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutyalmide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkyamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α,-dimethyl-hydroxyethylamide. Amides within the scope of dhydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula —NR$_{53}$COR$_{51}$ are methylcarbonylamide, ethylcarbonylamide, phenylcarbonylamide, and benzylcarbonylamide.

(4) Amides within the scope of sulfonylamino of the formula —NR$_{53}$SO$_2$R$_{51}$ are methylsulfonylamide, ethylsufonylamide, phenylsulfonylamide, p-tolysulfonylamide, benzylsulfonylamide.

Examples of alkyl of one to 12 carbon atoms, inclusive, are methyl, ethyl, propyl, isopropyl, isobutyl, tert-butyl, isopentyl, neopentyl, butyl, pentyl, hexyl, heptyl, octyl, nonyl, decyl, undecyl, dodecyl, isomeric forms thereof.

Examples of (C$_3$–C$_{10}$) cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of (C$_7$–C$_{12}$) aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

The compounds of Formula I produce certain prostacyclin-like pharmacological responses. Accordingly, the novel formula I compounds are useful as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and as antithrombotic agents as indicated below.

(a) Platelet Aggregation Inhibition

The compounds of Formulas I are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascualr diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2–4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 µg per ml of whole blood. The compounds of the present invention are useful in the treatment of peripheral vascular diseases, in the same manner as described in U.S. Pat. No. 4,103,026.

(b) Gastric Secretion Reduction

Compounds of Formula I are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 µg to about 20 µg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 0.001 to 100 mg per kg of body weight per day is employed. Once healing of the ulcers has been accomplished the maintenance dosage required to prevent recurrence is adjusted downward so long as the patient or animals remains asymptomatic. The compounds of specific Examples 5 and 6 set forth below demonstrate good cytoprotective properties with very low blood pressure effects in the rat and thus represent preferred compounds of the present invention. The product of Example 7 also represents a preferred compound of the present invention.

(c) NOSAC-Induced Lesion Inhibition

Compounds of Formula I are also useful in reducing the undesirable gastrointestinal effects resulting from systemic administration of anti-inflammatory prostaglandin synthetase inhibitors, and are useful for that purpose by concomitant administration of said compounds of Formula I and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula I compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formula I are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the avove use Formula I compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula I compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy and composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When Q is —COOR$_1$, the novel Formula I compounds so described are used for the purposes described above in the free acid form, in ester form, or in pharmacologically acceptable salt form. When the ester form is used, the ester is any of those within the above definition of R$_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula I for the purposes described above are those with pharmacologically acceptable metal cations, ammonia, amine cations, or quaternary ammonium cations. Illustrative pharmacological acceptable cations which R$_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphtic, cycloaliphatic, araliphtic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglycosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When Q is $-CH_2NL_2L_3$, the Formula I compounds so described are used for the purposes described in either free base or pharmacologically acceptable acid addition salt form.

The acid addition salts of the 2-decarboxy-2-aminomethyl- or 2-(substituted aminomethyl)- Formula I compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula I with the stoichiometric amount of the acid corresponding to the pharmacologically acceptable acid addition salt.

To obtain the optimum combination of biological response specificity, potency, and duration of activity, certain compounds within the scope of this invention are preferred. Preferred compounds of the present invention are Formula I compounds wherein $Z_4$ is $-CH_2-$, and of these compounds those wherein Y is $-SCH_2-CH_2CH_2-$, $-C\equiv C-$ or trans-$CH=CH-$ and/or Q is $-COOR_1$ are preferred especially when $R_1$ is hydrogen, methyl, ethyl, or a pharmacologically acceptable cation such as sodium. Compounds of Formula I wherein $C(L_1)R_7$ is definition (5) or (7) wherein X is $-O-$, or is definition (4) wherein $X_1$ is $=O$; $\alpha-OH$, $\beta-H$, or F,F are also preferred as are compounds wherein $-C(M_1)-C(L_1)R_7$ is definition (4) wherein p is 5.

In describing the preparation of the compounds of the present invention reference is made to Chart A to Chart H. In the Charts the various substituent groups have the following meanings. In Chart A: $R_7$, $L_{60}$, $Z_4$, $X_1$, $L_{20}$, $M_1$, and $L_1$ have the meanings defined in Formula I; $R_{70}$ is the same as $R_7$ except that when $-C(L_1)R_7$ is definition (4), $X_1$ is ethylenedioxy, or in other words $X_1$ is carbonyl protected as a ketal; alkyl is a hydrocarbon chain of from 1 to 4 carbon atoms and is straight or branched, e.g., methyl, ethyl, etc.; $Y_2$ is $-CH_2CH_2-$ or $-SCH_2-$; $M_2$ is $=O$ protected as a ketal, $\alpha-H$: $\beta-OR_x$, $\alpha-OR_x:\beta-H$, or H,H where $R_x$ is a protecting group as defined below; $M_4$ is $=O$; H,H; $\alpha-H,-\beta-OR_x$; $\alpha-OR_x,\beta-H$; $L_2$ is the same as $L_1$ in Formula I only any hydroxyl groups are protected as $OR_x$ where $R_x$ is as defined below; $L_{21}$ is the same as $L_{20}$ in Formula I only $L_{21}$ is not $=O$ and any hydroxyl groups are protected as $OR_x$ where $R_x$ is as defined below; $L_{22}$ is the same as $L_{20}$ in Formula I only any hydroxyl groups are protected as $OR_x$ where $R_x$ is as defined below; and $W_1$ has the meaning defined in Chart A. In Chart B: $W_2$ has the meaning defined in Chart B; $L_{60}$ and $R_7$ have the meanings defined in Formula I; $Y_3$ is $-CH_2CH_2-$, cis-$CH=CH-$, trans-$CH=CH-$ or $-C\equiv C-$; alkyl, $L_2$ and $L_{22}$ have the meanings defined above in Chart A; $M_3$ is $\alpha-H:\beta-OH$ or $\alpha-OH:\beta-H$; $M_1$ is $=O$, $\alpha-H:\beta-OR_x$, $\alpha-OR_x:\beta-H$, or H,H; Ra is the same as $R_7$ in Formula I only Ra is not $-C(CH_3)(OCH_3)-(CH_2)_n-CH=C(CH_3)_2$; Rb is $-C(CH_3)(OCH_3)-(CH_2)_nCH=C(CH_3)_2$ wherein the double bond is protected by bromine or an epoxide group; Rc represents $-C(CH_3)(OCH_3)-(CH_2)_n-CH=C(CH_3)_2$; and Rd represents $-C(CH_3)(OCH_3)-(CH_2)_n-CH=C(CH_3)_2$ only the double bond is protected with an epoxide function. In Chart C: $L_{60}$ is as defined in Formula I and $L_{22}$ has the meaning defined in Chart A above. In Chart D: Ph is phenyl; $L_{60}$ has the meaning defined in Formula I; and $L_{21}$ is as defined in Chart A above. In Chart E: Ph is phenyl; $L_{60}$, $M_1$, $L_1$, $R_7$, $Z_4$ and $X_1$ have the meanings defined in Formula I; $Y_3$ has the meaning defined in Chart B; and $L_{22}$ has the meaning defined in Chart A above. In Chart F the groups $Y_2$, $L_2$, $M_2$ and $R_7$ have the meanings defined in Chart A and alkyl has from 1 to 4 carbon atoms. In Chart H, $R_{71}$ is any of groups $R_7$ or $-C(L_1)R_7$ defined in Formula I.

During the preparation of the compounds of the present invention it may be necessary or desirable to protect the various hydroxyl groups at positions 11, 15, 16 or those contained in substituent $R_7$ as $OR_x$ groups where $R_x$ is a suitable protecting group. Many suitable protecting groups are known in the art and are described, for example in U.S. Pat. No. 4,401,824, particularly column 11, line 21 through column 13, line 15, wherein such groups are described as in the manner of adding and removing such groups on the hydroxyl. The aforesaid portions of U.S. Pat. No. 4,401,824 are incorporated herein by reference. Although any of these protecting groups may be employed those preferred are tetrahydropyranyl (THP), tetrahydrofuran (THF), tert-butyldimethylsilyl and tert-butyldiphenylsilyl. It may be useful, of course, to use protecting groups which may be hydrolyzed selectively and also when group $R_7$ contains an hydroxyl to be protected generally this hydroxyl is protected using the same type of group that is used at positions C-11, C-15 or C-16.

The compounds of the present invention are prepared by various means utilizing 2,3,3A,4-tetrahydro-5-methoxy-2-oxo-naphtho[2,3-B]furan depicted as Formula II. Although in describing the preparation of the compounds of Formula I only one optical enantiomer may be depicted the processes are applicable to both the D and L optical isomers or mixtures thereof unless, of course, a particular step is steroselective. The compounds of Formula I wherein $Y_1$ is $-CH_2CH_2-$ or $-SCH_2-$ are prepared as depicted in Chart A. The enollactone (II) is alkylated with two equivalents of a phosphonate anion (III) followed by one equivalent of acetic acid after which the reaction is warmed to effect the intramolecular Wadsworth-Emmons reaction, this procedure being an improved modification of the procedure of C. A. Henrick, et al., J. Am. Chem. Soc. 90, 5926 (1968). The resulting enone (IV) is reduced to the ketone (V) by procedures known in the art. For example the enone is hydrogenated over palladium catalyst in ethanol at 3 atmospheres pressure and may be followed by oxidation if necessary using, for example, Jones reagent. Equilibration to the thermodynamically favored ketone is achieved typically under basic conditions using, for example, potassium hydroxide in ethanol by procedures known in the art. When in compounds of Formula IV $R_7$ is a group containing a double bond such double bond is protected prior to reduction of the enone. For example the double bond can be protected by treatment of compound IV with one equivalent of bromine in carbon tetrachloride and following reduction of the enone and conversion (see below) to intermediate VI. The double bond is deprotected by treatment of V or VI with, e.g., zinc in acetic acid or ethanol. Also the double bond can be protected by treatment of compound IV with meta-chloroperbenzoic acid (MCPBA) in methylene chloride to give an epoxide which can be removed, restoring the double bond following reduction of the enone and conversion (see below) to intermediate VI, by treatment with tri-n-butylphosphine with heating (see M. J. Boskin and D. B. Denney, Chem. Ind. (London), 330, 1959) or treatment with tungsten hexachloride and lithium iodide with heating (see K. B. Sharpless, et al., J. Am. Chem. Soc. 94, 6538 (1972). The ketone (V) is then used to prepare compounds of Formula I or the intermediates (VI) which are utilized in preparing compounds of Formula I.

To prepare intermediates (VI) wherein $L_{21}$ is $\alpha$—H,-$\beta$—OH or $\alpha$—OH,$\beta$—H the ketone (V) is reduced by procedures known in the art, for example using sodium borohydride. Conversion of the ketone (V) to the intermediate (VI) where $L_{21}$ is methylene, i.e., $=CH_2$, typically is achieved via a Wittig-type procedure, for example, using methylenetriphenylphosphorane by generally known procedures. The methylene intermediate can be used to prepare compounds IX as depicted in Chart A or can be reduced to the corresponding compound wherein $L_{21}$ is $\alpha$—$CH_3$,$\beta$—H, for example, via hydrogenation over palladium catalyst by procedures known in the art. The methylene intermediate can also be used to prepare the corresponding compound wherein $L_{21}$ is $\alpha$—$CH_2OH$,$\beta$—H by hydroboration using, for example, 9-borobicyclononane (9-BBN) followed by workup with basic hydrogen peroxide. The intermediates of (VI) wherein $L_{21}$ and $L_{60}$ taken together form a double bond are prepared by treating the ketone (V) with a hydrazine derivative, such as, tosylhydrazine, followed by a Shapiro reaction on the resulting tosylhydrazone (see R. H. Shapiro, Chapter 3 in Organic Reactions, Volume 23, pp. 405-507). The 10,11-didehydro intermediate thus obtained can be used to prepare compounds (IX) as depicted in Chart A or can be hydrogenated, e.g., using palladium over charcoal, to intermediates (VI) wherein $L_{21}$ is H,H.

Following the various conversions at the 11-position the ketal of $R_{70}$ can be hydrolyzed typically with aqueous acid which will also remove any hydroxyl protecting groups in $M_2$ or hydrolyze the $M_2$ ketal. The $M_2$ hydroxyl groups can be reprotected at this point if necessary. Once the $R_{70}$ ketal is hydrolyzed compounds of Formula V and VI wherein —$C(L_1)R_7$ is 4-oxocyclohexyl can be used to prepare the corresponding compounds wherein —$C(L_1)R_7$ is 4-hydroxycyclohexyl or 4-difluorocyclohexyl. For example, to obtain compounds of Formula VI wherein —$C(L_1)R_7$ is 4-difluorocyclohexyl the corresponding 4-oxocyclohexyl compound is fluorinated using, e.g., diethylaminosulfur trifluoride by procedures known in the art. Any hydroxyl compounds present in the compound VI should be protected during the fluorination step. To obtain compounds of Formula VI wherein —$C(L_1)R_7$ is 4-hydroxycyclohexyl the corresponding 4-oxocyclohexyl compound is reduced, using, e.g., sodium borohydride.

The compounds of (V) and (VI) are converted to the phenols (VII) by, for example, treatment with lithium diphenylphosphide in tetrahydrofuran as generally described by R. E. Ireland and D. M. Walba, Tetrahedron Letters, 1071 (1976). Other methods for aryl methyl ether cleavages are known and may be employed, e.g., see M. V. Bhatt and S. U. Kulkarni, Synthesis 249 (1983). The phenols are converted to compounds (VIII)(a) by selective alkylation, for example, using potassium carbonate and a nitrile of the formula Cl—$Z_4$—CN wherein $Z_4$ has the meaning defined in Formula I by procedures generally known in the art. The phenols are converted to compounds (VIII)(b) by treatment with one equivalent of base, e.g., sodium hydride, and an appropriate halo alkanoate, e.g., alkyl bromo alkanoate of the formula Br$Z_4$—COOalkyl wherein alkyl has, e.g., from 1 to 4 carbon atoms and $Z_4$ has the meaning defined in Formula I. The compounds (VIII)(a) and (b) are hydrolyzed to the corresponding carboxylic acids of (VIII)(c) by procedures known in the art, for example, by using aqueous potassium hydroxide in methanol. The carboxylic acids of (VIII)(c) are converted to the final products (IX) wherein Q is COOH upon hydrolysis of any protecting groups at positions 11, 15 or 16 and the ketal protecting the C-15 is carbonyl. The carboxylic acids of (VIII)(c) can also be converted to compounds IX wherein Q is other than COOH by conventional means. For example, the carboxylic acid derivative can be reduced to (IX) wherein Q is —$CH_2OH$ by treatment with lithium aluminum hydride. The thus formed C-1 alcohols, i.e., compounds IX wherein Q is $CH_2OH$ can be oxidized to the corresponding carboxaldehyde which on treatment with a salt of hydroxylamine gives the oxime which is dehydrated to give the nitrile, i.e., compounds (IX) wherein Q is CN. The carboxylic acid derivative also can be converted to the various esters and amides defined in Formula I, and the amides can be reduced to the corresponding amines by using lithium aluminum hydride as generally described in U.S. Pat. No. 4,073,808. Following the conversions to the various Q groups any protecting groups present at C-11, C-15 or C-16 may be removed by hydrolysis as described hereinabove.

Compounds of Formula I wherein $Y_1$ is other than —$SCH_2$— are prepared using the aldehyde depicted in Chart B as Formula XI. By the procedures generally described in Chart U of U.S. Pat. No. 4,306,075 the Formula XI aldehyde is reacted with an alkyl phosphonate of Formula X under the conditions of a Wittig reaction to give a ketone of Formula XII. The ketone can be used to prepare final products of Formula I or can be reduced by hydride reduction to the trans-vinyl $\alpha$- or $\beta$-alcohol, i.e., compounds of formula XIII wherein $M_3$ is $\alpha$—OH,$\beta$—H or $\alpha$—H,$\beta$—OH. The trans-vinyl alcohol of XIII can be used to prepare final products of Formula I or when $R_7$ is other than —$C(CH_3)(OCH_3)$—$(CH_2)_n$—CH=$C(CH_3)_2$ can be hydrogenated to give compounds of Formula XIV. If prior to the initial reaction of the aldehyde of Formula XI and the phosphonate X any double bond present in the group $R_7$ is protected, as for example by treatment with one equivalent of bromine or by treatment with MCPBA as generally described hereinabove in connection with compounds of Formula IV in Chart A, the corresponding compounds of Formulas XII(a), XIII(a) and XIV(a) are obtained. Thus the compounds of Formula XIV(a) can be deprotected by treatment with zinc in acetic acid or ethanol when halogen protection is employed or by treatment with tributylphosphine or tungsten hexachloride and lithium iodide when epoxide protection is employed to give compounds of Formula XV. The compounds of Formulas XII and XIII wherein $R_7$ is other than a group containing unsaturation and of Formulas XII(a) and XIII(a) can be dihalogenated at C-13, C-14 and subsequently dehydrohalogenated by procedures well known in the art, e.g., see U.S. Pat. No. 4,029,681 or C. Gandolfi, et al., Il Farmaco, Ed. Sci. 27, 1125 (1972), to give compounds of Formula XVI wherein $R_7$ has the meaning defined in Formula I and of Formula XVI(a). The compounds of Formula XVI can be used to prepare final products of Formula I or the compounds of Formulas XVI and XVI(a) can be hydrogenated using a Lindlar catalyst to give the cis-vinyl alcohols of Formulas XVII and XVII(a). The compounds of Formula XVII can be used to prepare final products of Formula I or can be selectively oxidized to the cis-vinyl ketones of Formula XVIII using, e.g., DDQ or manganese dioxide by procedures known in the art. The epoxides of Formula XVII(a) can be treated with tributylphosphine or tungsten hexachloride and lithium iodide as described hereinabove to remove the epoxide protecting groups. When $R_5$ in the $M_1$ substituent of Formula I is methyl the appropriate starting materials are obtained by oxidizing the alcohols of Formulas XIV, XV and XVI to the corresponding ketones by procedures known in the art and then the resulting ketones as well as the vinyl ketones of Formulas XII and XVIII are treated with methyl lithium or a methyl Grignard by well known procedures. The compounds of Formulas XIII, XIV, XV, XVI and XVII wherein $M_3$ is $\alpha$—H,$\beta$—OH or $\alpha$—OH,$\beta$—H can be treated with a leaving group, e.g., converting the $M_3$ OH to OTs followed by a displacement reaction, e.g., with lithium aluminum hydride, to give the corresponding compounds wherein $M_3$ is H,H.

Collectively and for convenience all the starting materials prepared in connection with Chart B are depicted by Formula XIX in Chart B wherein $M_1$, $L_{60}$, and $R_7$ have the meanings defined in Formula I; $M_3$ is $\alpha$—H,$\beta$—OH or $\alpha$—OH,$\beta$—H; and $L_2$ and $L_{22}$ are the same as $L_1$ and $L_{20}$ respectively in Formula I only any hydroxyl group present is protected. The compounds of Formula XIX are converted to final products of Formula I by the same procedures set forth in Chart A for converting compounds VI and V to compounds IX. Prior to making these conversions any hydroxyl groups at positions 11, 15, 16 or in the $R_7$ group can be protected as ORx as described hereinabove.

The compounds of Formula XI are prepared as set forth in Chart C and Chart D. In Chart C the 2,3,3A,4-tetrahydro-5-methoxy-2-oxo-naphtho[2,3-B]furan (Formula II) is treated with the anion of trimethylphosphonoacetate followed by cyclization as generally described in connection with the reaction of compounds of Formulas II and III in Chart A. Alternatively the lactone (II) is treated at low temperature with the anion of methyl acetate (or ethyl acetate to give the ethyl ester analog) followed by warming to effect the cyclization. Compounds XX are reduced to the ketone XXI by means known in the art, e.g., by hydrogenation using palladium catalyst. The ketone XXI is reduced to the C-11 alcohol by, e.g., treatment with sodium borohydride after which the carboxy ester is reduced to the hydroxymethyl compound of formula XXII using, e.g., excess diisobutylaluminum hydride. The compound of formula XXII is converted to the aldehyde of formula XI by procedures known in the art, e.g., by protection of the C-13 alcohol with an ORx group followed by oxidation of the C-11 alcohol to the ketone, e.g., with Collins reagent, followed by conversion of the C-11 ketone to any of the $L_{22}$ groups as previously described, hydrolysis of the C-13 protecting group and oxidation to the aldehyde.

In Chart D the lactone II is alkylated with the anion of dimethylphosphate in a manner similar to that described for the reaction of compounds II and III in Chart A. The enone of Formula XXIII is reduced, e.g., by hydrogenation at room temperature over palladium catalyst by procedures known in the art to give the ketone of formula XXIV the ketone enolate of which is alkylated using benzylchloromethyl ether by procedures well known in the art to give compounds of Formula XXV wherein Ph is phenyl. The ketones of Formula XXV are converted to the various C-11 analogs of Formula XXVI by the same general procedures described for the conversion of compounds V to compounds VI in Chart A. Any hydroxyl group present at the C-11 substituent is protected appropriately as described hereinbefore prior to proceeding to compounds of Formula XXVII. Cleavage of the benzyl ethers of Formula XXVI by hydrogenation, procedures known in the art, gives the 12-hydroxymethyl compounds of Formula XXVII which are oxidized to the aldehydes of Formula XI using Collins reagent by known procedures.

The compounds of Formula IV in Chart A can also be prepared as depicted in Chart F. The 2,2-ethylenedioxy-5-methoxynaphthalen-3-ylacetic acid (Formula XXXVI) is reacted with two equivalents of a phosphonate of Formula III as generally described in connection with the preparation of compounds of Formula IV in Chart A to give the compounds of Formula XXXVII. The Formula XXXVII compound is deketalized by means known in the art, e.g., by treatment with aqueous acid followed by reprotection of any hydroxyl groups in the —C($M_2$)C($L_2$)$R_7$ chain as generally described herein. The ketone of Formula XXXVIII is then treated with base, e.g., sodium hydride in glyme to give the enone of Formula IV.

Compounds of Formula I wherein $Y_1$ is other than —SCH$_2$— can also be prepared as depicted in Chart E. Compounds XXVIII are obtained as depicted in Chart D (see Compounds XXV and XXVI) and are converted to the phenols of Formula XXIV by cleavage of the methyl ether using lithium diphenylphosphide in tetrahydrofuran as generally described hereinabove in connection with the preparation of compounds VII in Chart A. The phenols of Formula XXIX are converted to the compounds of XXX by the general procedures described in connection with the compounds of Formula VII to compounds of Formula IX in Chart A. The compounds of Formula XXX are converted to the aldehydes of Formula XXXIV by the general procedures described in connection with the preparation of compounds XI from compounds XXVI in Chart D, and the aldehydes of Formula XXXIV in turn are converted to the compounds of Formula XXXV by the general procedures described in Chart B for preparing compounds XIX.

Compounds of Formula I also can be prepared as depicted in Chart E beginning with compounds of Formula XXXI which are obtained as described in Chart C (see Formulas XXI and XXII). Cleavage of the methyl ether of XXXI is accomplished using lithium diphenylphosphide in tetrahydrofuran as described hereinbefore followed by acid esterification, e.g., with diazomethane, and the resulting phenols (XXXII) are converted to the compounds of Formula XXXIII by the general procedures described in connection with the conversion of compounds VII to compounds IX in Chart A. The compounds of XXXIII are then converted to the corresponding aldehydes of XXXIV as generally described in Chart C (i.e., XXII to XI).

The compounds of Formula I wherein

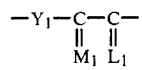

taken together is $$-CH=NNHC(=O)-NH-$$

are prepared by treating an aldehyde of Formula XXXIV (see Chart E) with a semicarbazide of the formula H$_2$NNHC(=O)NH—R$_7$ by procedures known in the art. The semicarbazides are obtained by procedures generally known in the art by converting an R$_7$CHO compound to the corresponding imine which is reduced to an amine. The amine is treated with dimethylcarbonate to give the corresponding carbamate which is treated with hydrazine hydrate to give the semicarbazide.

The phosphonates of Formulas III (Chart A) and X (Chart B) are known in the art or are prepared by procedures known in the art (see, for example, U.S. Pat. Nos. 4,029,681 and 4,401,824. Additionally in Charts G and H methods for obtaining appropriate phosphonates are described.

Chart G depicts the preparation of the appropriate phosphonate useful in obtaining compounds of Formula I wherein —C(M$_1$)C(L$_1$)R$_7$ taken together is

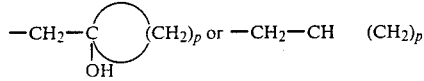

wherein p is 5. In Chart G cyclohexanone (1) is reacted with 3-carboxypropyltriphenylphosphorane under conditions of a Wittig reaction by known procedures. The resulting acid (2) is reduced to the alcohol (3) by known procedures, e.g., using lithium aluminum hydride. The alcohol is converted to the corresponding halide using, e.g., triphenylphosphine and carbon tetrachloride to give compound 4a or by tosylation followed by tosylate displacement with sodium iodide to give compound 4b by known procedures. The halide is treated with trimethylphosphite under conditions of an Arbuzoz reaction by known procedures to give the phosphonate 5 the use of which in preparing compounds of Formula I is further depicted in Chart G. The anion of compound 5 is formed, e.g., by treatment with butyl lithium, and the anion is reacted with compound II (Chart A) in the same manner as compounds III and II are reacted in Chart A. The resulting enone 6 can be reduced to the alcohol, compound 7, by the procedures described in connection with converting compounds of Formula IV to compounds of Formula VI wherein L$_{21}$ is hydroxyl in Chart A. Or, the enone 6 can be subjected to oxymercuration and reduction using, e.g, mercuric acetate followed by sodium borohydride, to give the enone 8 which in turn can be reduced to give compound 9 by the same means as compound 6 is reduced. Compound 6 can also be converted in compound 9 by selective epoxidation of the side chain olefin to an epoxide, using for example meta-chloroperbenzoic acid in methylene chloride. The resulting monoepoxide can then be hydrogenated as previously described, treated with sodium borohydride to reduce the C-11 ketone, and then treated with lithium aluminum hydride in tetrahydrofuran for example to reduce the epoxide. The alcohols 9 can be dehydrated to give a mixture of compounds wherein —C(M$_1$)C(L$_1$)R$_7$ is

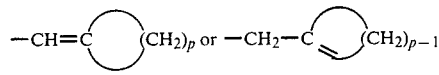

which compounds are separated by chromatographic procedures. Of course, it is readily apparent that the various C-11 position conversions described in connection with compounds of Formula V to give compounds of Formula VI in Chart A may be performed in the same manner on the intervening C-11 ketone formed upon reduction of the enone. Compounds 7 and 9 are then treated in a manner as described in connection with compounds of Formula VI (Chart A) to obtain compounds of Formula I. By substituting an appropriate cycloalkanone for cyclohexanone other compounds of Formula I wherein p is other than 5 are obtained.

In Chart H the aldehyde (11) is alkylated with vinyl Grignard or vinyl lithium to give the vinyl alcohol (15) by procedures known in the art. Kinetic resolution of the vinyl alcohol (15) to give compound (16) is accomplished by the method of Sharpless (Martin, V. S., et al., J. Am. Chem. Soc. 103, 6237 (1981). Alternatively, the aldehyde is alkylated with acetylene anion by known procedures to give the ethynyl alcohol (12) which is oxidized to the ketone (13) using, e.g., Jones reagent, by known procedures. The ketone (13) is reduced assymetrically using chiral reagents by known procedures. See e.g., Midland, M. M., J. Org. Chem. 47, 2815 (1982); J. Org. Chem. 46, 3933 (1981), and J. Am. Chem. Soc. 102, 867 (1980); and also, Cohen, N., J. Org. Chem. 45, 583 (1980) and Brinkmeyer, R. S., and Kapoor, V., J. Am. Chem. Soc. 99, 8339 (1977). The ethynyl alcohol (14) is then partially reduced using, e.g., sodium bis(2-methoxyethoxy)aluminum hydride in toluene or hydrogenation over a Lindlar catalyst by known procedures. The vinyl alcohol (16) is then protected, e.g., as a tetrahydropyranyl group and either subjected to iodoboration by the general procedures of H. C. Brown, "Organic Synthesis via Boranes," John Wiley, N.Y., 1975, pp. 101-102, to give compound (21) or is subjected to hydroboration and oxidation using, e.g., 9-borabicyclononane followed by alkaline peroxide work-up by known procedures to give 3-R$_{71}$-3-OR$_x$-propanol. The propanol is converted to compound 21 by direct replacement of the primary OH with iodide using iodine and a triaryl phosphine as generally described by B. R. Castro, "Organic Reactions," 29, p. 1, ed., W. G. Dauben, John Wiley, N.Y., 1983. Alternatively the primary OH of the propanol is selectively activated, e.g., via tosylation, followed by displacement of the tosylate with iodide in acetone and diisopropylamine to give compound (21). Compound (21) is treated with the anion of dialkyl methyl phosphonate to give compound (22).

As depicted in Chart H, the protected vinyl alcohol (17) may also be converted to the alcohol (18) by, e.g., ozonolysis and treatment with a reducing agent such as sodium borohydride. The alcohol (18) can be converted to the iodide (19) directly or via the tosylate as described above in connection with the preparation of compound (21). The iodide (19) is then alkylated with a dialkyl methylthio phosphonate following the general methods outlined by M. Mikolajck, et al., J. Org. Chem. 44, 2967 (1979) to give compound (20).

The various aldehydes, compounds (11), utilized in Chart H are known in the art or are obtained by means known in the art. Illustratively, 4-tetrahydropyrancarboxaldehyde is obtained by ketone homologation of 4-tetrahydroopyranone, e.g., using methoxymethyltriphenylphosphorane followed by aqueous acid enol ether hydrolysis by procedures known in the art. 2-Tetrahydropyrancarboxaldehyde is obtained by oxidizing 2-tetrahydropyranylmethanol using, e.g., oxalyl chloride and dimethyl sulfoxide in methylene chloride by known procedures. When —C($L_1$)$R_7$ is 4-cyclohexanone, one of the carbonyl groups of cyclohexan-1,4-dione is protected as a ketal following procedures known in the art and the remaining carbonyl is subjected to homologation as generally described hereinabove. 2-Piperidine methanol, which is commercially available, can be oxidized, e.g., using Cornforth procedure, to 2-piperidinecarboxaldehyde the nitrogen of which is protected, e.g., with a trimethylsilyl group prior to converting the to phosphonate by known procedures. Also commercially available is 4-piperidone monohydrate hydrochloride which can be converted to 4-piperidinecarboxaldehyde by treatment with one equivalent of base, followed by homologation of the ketone as described hereinabove. Prior to converting 4-piperidinecarboxaldehyde to an appropriate phosphonate the nitrogen is protected with, e.g., trimethylsilyl. 4-Tetrahydrothiopyranone is commercially available and can be converted to 4-tetrahydrothiopyrancarboxaldehyde by homologation as described hereinabove. Other suitable aldehydes may be prepared by analogous methods or other means readily apparent to one skilled in the art.

The compound of Formula II is prepared as described in Example 1.

Optically pure compounds of Formula I wherein $L_{20}$ is α—OH:β—H are obtained by attaching a chiral ester or chiral carbamate, e.g., using (+)-α-methoxy-α-trifluoromethylphenyl acid chloride or (+)-α-methylbenzyl isocyanate to a compound of Formula VI depicted in Chart A using procedures known in the art giving a product which permits separation of the diastereomers. Following separation of the diastereomers the compounds are subjected to ester hydrolysis by well known procedures, e.g., using potassium carbonate in methanol or potassium hydroxide in water and methanol. The resolved diastereomers are then converted to the final products of the invention as depicted in Chart A proceeding from compounds of Formula VI to compounds of Formula IX. Alternatively, these optically pure compounds are obtained by reduction of the ketone depicted as Formula IV in Chart A to the corresponding alcohol i.e. 11-OH compound, by procedures well known in the art, e.g., using sodium borohydride in ethanol, followed by attachment of a chiral ester or a chiral carbamate as described above with subsequent separation of the diastereomers and ester hydrolysis. The resulting resolved diastereomers are then oxidized using e.g., manganese dioxide, or dimethylsulfoxide and dicyclohexylcarbodiimide to give a resolved ketone corresponding to Formula IV in Chart A which when treated as described in Chart A in going from Formula IV through Formula IX gives resolved compounds of the invention. Additionally, compounds of Formula I wherein $L_{20}$ is OH,H can be resolved by e.g., treatment with (+)-α-methylbenzylamine by procedures known in the art to give a chiral amide followed by amide hydrolysis using, e.g., potassium hydroxide in water and methanol at reflux.

EXAMPLE 1

2,3,3A-4-Tetrahydro-5-methoxy-2-oxo-naphtho[2,3-B]furan (a)

3,4-Dihydro-2-hydroxy-5-methoxynaphthalenecarboxylic acid methyl ester

A solution of 5-methoxy-β-tetralone (20.6 g, 117 mmol) and 350 ml of dimethylcarbonate was cooled to 0° to 5°, then treated with 32 ml (140 mmol) of 25% sodium methoxide in oxygen-free methanol. The resulting dark brown solution was stirred for 30 minutes at 0°, then heated to 70°, stirred for 18 hours under a nitrogen atmosphere, then cooled to 0° to 5° and quenched with 200 ml of cold 1N degassed aqueous hydrochloric acid. The solution was extracted with ethyl acetate (2×150 ml). The combined organic layers were washed with brine (2×200 ml), dried over magnesium sulfate, filtered, and rotary evaporated at 50°. The resulting red-brown oil was crystallized from 80 ml of 1:1 ether/hexane in the freezer to give 14.43 g (53%) of yellow crystals, m.p. 56°–58°. A second crop of yellow crystals (3.6 g, 14%) can be obtained from 20 ml 1:1 ether/hexane, m.p. 55°–58°. The mother liquor (~12 g) was chromatographed on 100 g of silica gel 60 slurry packed in 300 ml of hexane. Eluting with 2% ethyl acetate in hexane gave 5.1 g (19%) of the title compound (a) in fractions 17–28, m.p. 53°–58°. Total yield of compound (a) was 23.1 g (85%).

NMR (CDCl$_3$, TMS): δ 2.3–2.7 (m, 2H), 2.8–3.0 (m, 2H), 3.80 (s, 3H), 3.90 (s, 3H), 6.6–7.5 (m, 3H), 13.35 (s, 1H).

Infrared: $\nu_{max}$ (mull): 1640, 1598, 1587, 1566, 1422, 1378, 1311, 1277, 1220, 1207, 1086, 1052, 1030, 892, 787, 769, 721 cm$^{-1}$.

TLC (Silica Gel GF): Rf=0.47 in 10% ethyl acetate in hexane.

(b)

3,4-Dihydro-2-hydroxy-3-(3-propene)-5-methoxynaphthalenecarboxylic acid methyl ester A solution of 300 ml of tetrahydrofuran and 39 ml (282 mmol) of diisopropylamine under nitrogen was cooled to −50° C. and treated with 170 ml (272 mmol) of 1.6M n-butyllithium in hexane dropwise maintaining the temperature at −50° C. The solution was stirred at −50° for 15 minutes, then at 0° for 15 minutes. A solution of 30.0 g (128.1 mmol) of 3,4-dihydro-2-hydroxy-5-methoxynaphthalenecarboxylic acid methyl ester in 70 ml of tetrahydrofuran was added dropwise to maintain the temperature at 0°. The resulting yellow suspension was treated with 13.5 ml (160 mmol) of allyl bromide in 50 ml of tetrahydrofuran dropwise maintaining the temperature at 0°. The cooling bath was removed and the orange solution was stirred at ambient temperature for 1 hour, then cooled to 10° to 15° C. and 500 ml of 1N degassed aqueous hydrochloric acid was added dropwise maintaining the temperature below 15°. The layers were separated and the aqueous layer extracted with 400 ml of ethyl acetate. The organic layers were combined and washed with 500 ml of brine, dried over anhydrous magnesium sulfate, filtered and concentrated via rotary evaporation and then house vacuum to give 44.2 g of the title compound (b), m.p. 70°–71°.

NMR (CDCl$_3$, TMS): δ 1.8–3.2 (m, 5H), (3H singlets at 3.80 δ and 3.90 δ; 6H) 4.7–5.4 (m, 2H), 5.5–6.1 (m, 1H), 6.5–7.6 (m, 3H), 13.4 (s, 1H).

Infrared: $\nu_{max}$ 2925, 2956, 1237, 1598, 1440, 1270, 1257, 1051, 1002, 885, 790, 772 cm$^{-1}$.

TLC (Silica Gel GF): Rf=0.34 in 10% ethyl acetate in hexane.

(c)
1,2,3,4-Tetrahydro-5-methoxy-3-(3-propene)naphthalen-2-one

A mixture of 44.1 g of 3,4-dihydro-2-hydroxy-5-methoxy-3-(3-propene)naphthalenecarboxylic acid methyl ester and 110 ml of dimethyl sulfoxide was degassed with nitrogen and heated to ~50° under nitrogen to effect dissolution. The resulting orange solution was treated with 6.0 g (142 mmol) of anhydrous lithium chloride and 7.5 ml of deionized water and heated to 150° under nitrogen, then stirred at 150° for 4 hours. The solution was cooled to 10° to 15°, diluted with 500 ml of 1:1 brine/water and extracted with three 200 ml portions of ethyl acetate. The organic layers were combined and washed with three 200 ml portions of water, two 200 ml portions of brine, dried over anhydrous magnesium sulfate, filtered and concentrated in vacuo to give 28.3 g of the title compound (c), m.p. 39°–40°.

NMR (CDCl$_3$, TMS): δ 1.8–2.8 (m, 4H), 3.0–4.3 (m, including 2H broad singlet at 3.53 δ and 3H singlet at 3.80 δ, 6H), 4.8–5.4 (m, 2H), 5.5–6.1 (m, 1H), 6.5–6.4 (m, 3H).

Infrared: $\nu_{max}$ 2922, 1713, 1642, 1599, 1588, 1472, 1441, 1436, 1258, 1081, 910, 771, 719, 609 cm$^{-1}$.

TLC (Silica Gel GF): Rf=0.32 in 10% ethyl acetate in hexane.

(d) The 2-ethylenedioxy ketal of 1,2,3,4-tetrahydro-5-methoxy-3-(3-propene)naphthalen-2-one A solution of 27.8 g (128 mmol) of 1,2,3,4-tetrahydro-5-methoxy-3-(3-propene)naphthalen-2-one, 450 ml of methylene chloride, 150 ml (2.2 mol) of ethylene glycol, 60 ml (450 mmol) of triethylorthoformate, and 270 mg (1.41 mmol) of p-toluenesulfonic acid monohydrate was degassed with nitrogen and stirred at room temperature under nitrogen for 22 hours after which the reaction was quenched with 7.5 ml (52 mmol) of triethylamine, diluted with 500 ml of 1:1 saturated aqueous sodium bicarbonate/water and the layers were separated. The aqueous layer was extracted with 200 ml of methylene chloride. The combined organic layers were washed with three 500 ml portions of water and 500 ml of brine, then concentrated by rotary evaporation to give ~40 g of a red oil. The red oil was dissolved in 200 ml of hexane and treated with 200 ml of water. The mixture was degassed and stirred under nitrogen for one hour. The layers were separated and the organic layer was dried with anhydrous magnesium sulfate, then filtered and concentrated in vacuo to give ~35 g of an orange oil. The orange oil was filtered through 100 g of silica gel 50 washing with 800 ml of 10% ethyl acetate in hexane. The filtrate was concentrated in vacuo to give 31.5 g (94%) of the title compound (d), m.p. 34°–35°.

NMR (CDCl$_3$, TMS): δ 1.7–3.3 (m, including 2H broad singlet at 2.90 δ, 7H), 3.4–4.4 (m, including 3H at 3.77 δ, 7H), 4.8–5.3 (m, 2H), 5.6–6.2 (m, 1H), 6.5–7.4 (m, 3H).

Infrared: $\nu_{max}$ (film): 2940, 2890, 1620, 1590, 1470, 1440, 1260, 1155, 1075, 950, 770 cm$^{-1}$.

TLC (Silica Gel GF): Rf=0.35 in 10% ethyl acetate in hexane.

(e)
2,2-Ethylenedioxy-5-methoxy-1,2,3,4-tetrahydronaphthalen-3-ylacetic acid

To a mixture of 1400 ml of deionized water and 66.5 g (310 mmol) of sodium metaperiodate was added 1.0 g (6.4 mmol) of potassium permanganate. The purple solution was stirred for 30 minutes at room temperature then treated in sequence with 5.0 g (36 mmol) of anhydrous potassium carbonate, then 350 ml of t-butanol, followed by 8.9 g (34 mmol) of the ethylenedioxy ketal of 1,2,3,4-tetrahydro-5-methoxy-3-(3-propene)naphthalen-2-one in 350 ml of t-butanol. The resulting reddish-purple suspension was stirred at room temperature for 2 hours. The reaction was quenched with 10 ml (150 mmol) of ethylene glycol and stirred at room temperature for 2.5 hours. Approximately 30% of the solvent was removed via rotary evaporation, and the remaining material was acidified to pH 3–4 with 100 ml of 1M aqueous hydrochloric acid and extracted with three 500 ml portions of ethyl acetate. The organic layers were combined and washed with two 500 ml portions of brine, dried over anhydrous sodium sulfate, filtered, and the solvents removed in vacuo to give 8.5 g (89%) of the title compound (e), m.p. 129°–130°.

NMR (CDCl$_3$, TM): δ 1.8–3.4 (m, 6H), 3.9–4.5 (m, including 3H singlet at 3.77 δ, 8H), 6.4–7.4 (m, 3H), 10.27 (broad singlet, 1H).

TLC (Silica Gel GF): Rf=0.20 in 30% ethyl acetate in hexane.

(f)
5-Methoxy-2-oxo-1,2,3,4-tetrahydronaphthalen-3-ylacetic acid

A solution of 8.0 g (28.7 mmol) of 2,2-ethylenedioxy-5-methoxy-1,2,3,4-tetrahydronaphthalen-3-ylacetic acid, 80 ml of 3N aqueous hydrochloric acid, and 80 ml of acetone was degassed and heated to 60° under nitrogen then stirred under nitrogen at 60° for 4 hours. The reaction was cooled to room temperature, approximately 50% of the solvent was removed by rotary evaporation, diluted with 100 ml of brine, and extracted with three 100 ml portions of ethyl acetate. The organic layers were combined and washed with two 100 ml portions of brine, dried over anhydrous sodium sulfate, filtered, and concentrated via rotary evaporation to give an orange solid. The orange solid was triturated with 10 ml of ether and filtered to give 4.9 g (73%) of the title compound (f), m.p. 129°–131°.

NMR (CDCl$_3$, TMS): δ 2.2–3.2 (m, 4H), 3.3–4.0 (m, including 2H broad singlet at 3.67 δ and 3H singlet at 3.85 δ, 6H), 6.4–6.9 (m, 2H), 7.1–7.3 (m, 1H), 10.2 (bs, 1H).

Infrared: ν$_{max}$ 2908, 2855, 1730, 1714, 1676, 1471, 1454, 1446, 1266, 1202, 1195, 1184, 1091, 776, 747, 724 cm$^{-1}$.

TLC (Silica Gel GF): Rf=0.22 in 35% ethyl acetate in hexane with 1% acetic acid.

(g) 2,3,3A,4-Tetrahydro-5-methoxy-2-oxo-naphtho[2,3-B]furan (Compound II)

A solution of 5-methoxy-2-oxo-1,2,3,4-tetrahydronaphthalen-3-ylacetic acid (1.75 g, 7.49 mmol) in 88 ml of ethyl acetate was treated all at once with 88 ml of a reagent prepared immediately before use as follows: 20.0 ml of a solution of 0.40 ml of 70% perchloric acid in 100 ml of ethyl acetate was added to 50 ml of ethyl acetate, then 19.2 ml (0.20 mmol) of acetic anhydride was added and the reagent diluted to a total volume of 100 ml with ethyl acetate. The solution was stirred for 10 minutes at room temperature under nitrogen then quenched with 100 ml of saturated aqueous sodium bicarbonate. The layers were separated and the organic layer was washed with 100 ml of brine, dried with anhydrous sodium sulfate, filtered and concentrated in vacuo. To remove the excess acetic anhydride, the red oil was treated with 10 drops of pyridine and 200 ml of methanol. The solvents were removed in vachuo (rotovap bath below 30°); then to remove the pyridine 100 ml of toluene was added and the solvents were removed in vacuo (rotovap bath below 35°). An additional 100 ml of toluene was added and concentrated in vacuo to give a yellow solid. The yellow solid was recrystallized from ethyl acetate and hexane to give 890 mg (55%) of the title compound (g), m.p. 130°–141°.

NMR (CDCl$_3$, TMS): δ 2.0–4.1 (m, including 3H singlet at 3.86 δ, 8H), 6.0–6.2 (d, J=3 Hz, 1H), 6.6–7.0 (m, 2H), 7.0–7.4 (m, 1H).

Infrared: ν$_{max}$ 2926, 1800, 1686, 1571, 1472, 1444, 1267, 1075, 964, 865, 850, 780 cm$^{-1}$.

CMC (CDCl$_3$, TMS): δ ppm (relative intensity): 173.94 (14), 156.31 (17), 154.89 (18), 134.98 (17), 127.79 (92), 121.42 (11), 119.48 (90), 109.60 (97), 101.09 (81), 55.48 (64), 34.76 (88), 33.17 (88), 27.29 (85).

TLC (Silica Gel GF): Rf=0.32 in 15% ethyl acetate in hexane.

EXAMPLE 2

4-(4-Tetrahydropyranyl)-4-hydroxydimethylbutylphosphonate tetrahydropyranylether A suspension of 40 g (116 mmol) of methoxymethyltriphenylphosphonium chloride in 400 ml of tetrahydrofuran was evacuated and flushed with dry nitrogen, cooled to −15° and treated slowly with 80 ml of 1.6M n-butyllithium in hexane. The orange-colored mixture was stirred 40 minutes longer at −15° and then treated with a solution of 5.0 g (50 mmol) of tetrahydro-4H-pyran-4-one in 50 ml of toluene. The color changed to a light orange-yellow. After 2 hours at −15° to −5°, the mixture was made slightly acidic with KHSO$_4$, brine was added, and the mixture extracted twice with ethyl acetate. The combined extract was washed with brine, dried over MgSO$_4$ and concentrated to an amber oil which partially crystallized on standing. Chromatography over 250 g of silica gel afforded 3.1 of crude product (eluted with 5% and 10% ethyl acetate in Skellysolve B (SSB)) as a colorless oil. A small portion was further purified over silica gel using 10% and 20% ether in SSB for elution.

TLC (silica gel): Rf 0.55 (50% ether in SSB).
NMR (CCl$_4$-TMS)δ: 5.8 (s, 1H), 3.2–3.7 (m, 7H), 2.1 (ch of t, J=7, 4H).

A solution of 3.1 g of 4-methoxymethylenetetrahydropyran in 50 ml of ether was mixed with 30 ml of 5% aqueous KHSO$_4$ and stirred vigorously for 3 days. The ether layer was separated. The aqueous layer was saturated with salt and extracted with ether. The ether extracts were combined, washed with brine, dried over MgSO$_4$ and concentrated to afford 1.62 g of colorless oil (28% overall from the ketone).

TLC (silica gel): Rf 0.33 (50% ether-SSB).
NMR (CCl$_4$-TMS)δ: 9.6 (s, 1H), 3.7 (m, 2H), 3.4 (m, 2H), 2.35 (septet, 1H), 1.2–2.0 (m, 4H).

A stirred solution of 2.5 g (17.6 mmol) of the aldehyde in 15 ml of anhydrous ether was flushed with dry nitrogen, cooled to 0° and treated dropwise in 5 minutes with 12 ml of 2M vinylmagnesium chloride solution in tetrahydrofuran. Initially a precipitate formed and then the mixture cleared. After 45 minutes at 0° to 5° the reaction was quenched with aqueous NH$_4$Cl, diluted with brine and extracted with ether and ethyl acetate. The combined extract was washed with brine dried over MgSO$_4$ and concentrated to afford 3.0 g of oil.

The total crude alcohol was dissolved in 25 ml of methylene chloride, treated with 7 ml of dihydropyran and 1 ml of a saturated solution of pyridine hydrochloride in methylene chloride and allowed to stand at room temperature overnight. The clear solution was then washed with NaHCO$_3$ solution, brine, dried over MgSO$_4$ and concentrated to an oil which was chromatographed from methylene chloride over 100 g of silica gel slurry-packed with SSB. The column was eluted with increasing concentration of ethyl acetate in SSB. The desired product was recovered from the 5% and 10% ethyl acetate eluent as colorless oil showing 2 close spots on TLC which seemed by NMR to be isomeric. Total yield 3.17 g.

A solution of 3.39 g of the vinyl compound in 50 ml of tetrahydrofuran was flushed with dry nitrogen, cooled to −15° and treated with stirring with 40 ml of a 0.5M solution of 9-borabicyclo[3.3.1]nonane in tetrahydrofuran. The addition required 10 minutes after which the mixture was kept at −15° for 30 minutes then −15° to +20° during the next 30 minutes. The mixture was again cooled in an ice bath and 40 ml of 1N NaOH added in portions during 3 minutes. This was followed by the portionwise addition (in 5 minutes) of 13 ml of 30% hydrogen peroxide. The mixture was stirred 30 minutes longer with cooling, then 20 minutes witout cooling. Dilute hydrochloric acid was added until slightly acidic, then brine, and the mixture extracted 3 times with ethyl acetate. The combined extract was washed with brine, dried over MgSO$_4$ and concentrated to a colorless oil. Chromatography from toluene solution over 200 g of silica gel afforded 3.25 g (eluted with ethyl acetate) of colorless oily product contaminated to a small extent (<10%) with a solid impurity.

A stirred solution of 3.25 g of the alcohol in 15 ml of pyridine was cooled in an ice bath and treated with 30 mg of dimethylaminopyridine and 3.5 g of tosyl chloride. A second portion of tosyl chloride (1.5 g) was added after 2 hours and cooling continued for 2 hours more. Lactic acid (2 ml of 87%) was added, and after 15 minutes, the mixture was diluted with brine and extracted 3 times with ethyl acetate. The combined extract was washed with cold KHSO4 solution, NaHCO3 solution, brine dried over MgSO4 and concentrated to give 4.1 g of colorless oil.

The total crude tosylate was dissolved in 75 ml of acetone, treated with 0.25 ml of diisopropylethyl amine and 7.5 g of powdered sodium iodide and stirred at room temperature for 6.5 hours. Dilute brine was added and the mixture extracted 3 times with ethyl acetate, washed with brine, dried with MgSO4 and concentrated to 4.1 g of colorless oil.

A stirred solution of 0.5 ml of diethylamine (redistilled) in 10 ml of tetrahydrofuran was flushed with dry nitrogen, cooled to −40° and treated with 3.2 ml of 1.55M n-butyllithium in hexane. The mixture was kept for 30 minutes at −35° to −40°, then further cooled to −78° and treated with a solution of 0.5 ml (0.57 g, 4.5 mmol) of dimethylmethylphosphonate in 5 ml of tetrahydrofuran after which a solution of 1.02 g of the iodo compound in 5 ml of tetrahydrofuran was added. The cloudy yellow mixture was stirred for 4 hours during which time the temperature was allowed to slowly rise to −10°. Dilute brine was then added, and the mixture extracted twice with ethyl acetate. The combined extract was washed with brine, dried over MgSO4 and concentrated to 1.35 g of yellow oil. Chromatography over 40 g of silica gel afforded 0.22 g of recovered iodo compound (eluted 10% acetone) in $CH_2Cl_2$ and 0.52 g of product (pale yellow oil eluted 40% acetone in $CH_2Cl_2$).

EXAMPLE 3

4-(2-Tetrahydropyranyl)-4-hydroxydimethylbutylphosphonate, tetrahydropyranyl ether A solution of 10 ml (110 mmol) of oxalyl chloride in 50 ml of methylene chloride was cooled in a −50° to −60° bath and treated dropwise with stirring with a solution of 17 ml (220 mmol) of dimethylsulfoxide in 50 ml of methylene chloride. The addition required 5 minutes, and the mixture was stirred 10 minutes longer. With continued cooling a solution of 10 g (56 mmol) of tetrahydrofuran-2-methanol was added in 5 and the now thickened mixture allowed to react for 15 minutes longer whereupon a solution of 35 ml (485 mmol) of triethylamine in 35 ml of methylene chloride was added. The mixture thickened further. After 10 minutes the mixture was warmed to room temperature for 10 minutes then diluted with brine. The methylene chloride layer was separated, washed with fresh brine, dried over MgSO4 and evaporated. The only residue was chromatographed over 250 g of silica gel slurry-packed with SSB. The column was eluted with 10% and 20% acetone in SSB. From the latter were obtained 5.9 g (58%) of aldehyde (colorless oil) followed by 0.9 g (9% of recovered starting material.

TLC (silica gel): $R_f$0.46 (aldehyde); $R_f$0.23 (alcohol) using 50% ether in SSB.

NMR (CCl4-TMS)δ: 9.6 (s, 1H, CHO), 4.0 (m, 1H), 3.6 (m, 2H), 1.1-2.0 (m, 6H).

A solution of 8.4 g (73.6 mmol) of aldehyde in 50 ml of anhydrous ether was flushed with dry nitrogen, cooled to 0° and treated dropwise with stirring with 44 ml of 2M vinyl magnesium chloride solution in tetrahydrofuran. After 40 minutes at 0.5 the reaction was quenched with aqueous ammonium chloride solution and brine. The ether layer was separated, and the mixture extracted twice more with ether. The combined extract was washed with brine, dried over MgSO4 and concentrated to 11.5 g of pale yellow oil.

The total crude alcohol was dissolved in 75 ml of methylene chloride, treated with 25 ml of dihydropyran and 4 ml of a saturated solution of pyridine hydrochloride in methylene chloride and kept at room temperature for 20 hours. The clear solution was then washed with NaHCO3 solution, brine, dried over MgSO4 and concentrated to an oil which was chromatographed over 250 g of silica gel slurry-packed with SSB. The column was eluted with 3% and 5% ethyl acetate in SSB to afford 8.9 g of product as a tlc-homogeneous oil. An additional 1.3 g of impure product was also obtained.

A solution of 8.9 g of the vinyl compound in 150 ml of tetrahydrofuran was flushed with dry nitrogen, cooled to −15° and treated with stirring with 100 ml of a 0.5M solution of 9-borabicyclo[3.3.1]nonane in tetrahydrofuran. The addition required 15 minutes after which the mixture was kept at −10° to −15° for 30 minutes then −10° to 20° in the next 30 minutes. The mixture was recooled to 0° and 100 ml of 1NaOH added in portions. This was followed by the portionwise addition of 32 ml of 30% hydrogen peroxide. The mixture was stirred for 20 minutes longer in the cooling bath, then 20 minutes without cooling. After being made slightly acidic by the nature of dilute hydrochloric acid, the mixture was diluted with brine and extracted with 3 portions of ethyl acetate. The combined extract was washed with brine, dried over MgSO4 and concentrated to a colorless oil, chromatographing over 250 g of silica gel afforded 2.14 g of unreacted starting material (eluted 10% ethyl acetate in SSB), and 7.30 g of a colorless oil (60% EtOAc-SSB).

A solution of 10.0 g of the alcohol in 45 ml of pyridine was cooled in an ice bath and treated with stirring with 90 mg of dimethylaminepyridne and 10 l g (52 mmol) of toluene sulfonyl chloride. After 2 hours an additional 4 g (20 mmol) of toluene sylfonyl chloride was added and stirring and cooling continued for 2 hours longer. Lactic acid (4 ml of an 8% solution) was added, and after 20 minutes brine was added, and the mixture extracted 3 times with ethyl acetate. The combined extract was washed with cold 10% KHSO4 solution, NaHCO3 solution, brine, dried with MgSO4 and concentrated to an amber oil. An IR spectrum showed no hydroxyl.

The total crude tosylate was dissolved in 125 ml of acetone, treated with 0.5 ml of diisopropylethyl amine amd 20 g of sodium iodide and stirred at room temperature for 6 hours. The mixture was diluted with dilute brine and extracted 3 times with ethyl acetate. The comtined extract was dried over MgSO4 and concentrated to afford 10.9 g of dark-yellow oil showing multiple spots on tlc (50% ether-SSB). The material was chromatographed from toluene over 250 g of silica gel slurry-packed with SSB.

A solution of 6.0 g (4.2 ml, 33.8 mmol) of dimethylmethylphosphonate in 40 ml of tetrahydrofuran was evacuated, flushed with dry nitrogen, cooled to −78° and treated with stirring with 29 ml of 1.6M n-butyllithium in hexane. After 30 minutes at −78° a solution of 4.3 g of the iodo compound in 20 ml of tetrahydrofuran was added. The mixture was stirred for 2 hours during which time the temperature was allowed to slowly rise to 0°. Acetic acid (3 ml) was then added, the now yellow mixture diluted with brine and extracted 3 times with ethyl acetate. The washed and dried extract was concentrated to 7 g of dark-yellow oil. Chromatography over 150 g of silica gel slurry-packed with methylene chloride afforded 0.81 g (eluted 10% acetone in $CH_2Cl_2$) of recovered starting material, 0.59 of an unknown (10% and 20% acetone in methylene chloride) and 3.30 g of colorless oil (20% and 40% acetone in methylene chloride).

EXAMPLE 4

9-Deoxy-13,14-dihydro-2',9α-methano-3-oxa-15-(4'-tetrahydropyranyl)-4,5,6,16,17,18,19,20-octanor-(1',3'-interphenylene)-$PGF_1$ (Formula I. $L_{20}$ is α-OH, β-H,

is 4'-tetrahydropyranyl, $M_1$ is α-OH,β-H, Q=$CO_2H$, $Z_4$ is —$CH_2$—, $Y_1$ is $CH_2CH_2$, and $L_{60}$ is H.

(a)
8,12-Didehydro-9,11-dideoxy-13,14-dihydro-2',9α-methano-3-oxa-11-oxo-15-(4'-tetrahydropyranyl)-1,4,5,6,16,17,18,19,20-nonanor-3,7-(1',3'interphenylene)-$PGF_1$,15-(tetrahydropyranyl ether A solution of 11.90 g of the product of Example 2 and 450 ml of dry tetrahydrofuran, degassed and flushed with nitrogen, was cooled to −78° C. The stirred solution was treated with 22.5 ml (36.0 mmol) of 1.60M n-butyllithium dropwise over 15 to 20 minutes then stirred for one hour at −78° C. A solution of 3.71 g (17.17 mmol) of 2,3,3A,4-tetrahydro-5-methoxy-2-oxonaphtho[2,3-B]furan in 70 ml of dry tetrahydrofuran, degassed and flushed with nitrogen and cooled to −78° C. under nitrogen, was added via cannula and under nitrogen pressure dropwise over 30 minutes. The resulting solution was stirred for 4 hours while allowing the temperature to rise slowly to −10° after which the solution was treated dropwise with 1.03 ml (18 mmol) of glacial acetic acid. The reaction mixture was stirred for 15 minutes at ambient temperature and heated at 60° to 65° for 6 hours. The resulting yellow-green solution was cooled to 5°, neutralized to about pH 6 to 7 with 500 ml of brine containing 18 ml (18 mmol) of 1M aqueous hydrochloric acid, and extracted with three 250 ml portions of ethyl acetate. The organic layers were combined and washed with 200 ml of 3:1 brine/saturated aqueous sodium bicarbonate and then with 400 ml of brine and dried over anhydrous sodium sulfate, filtered and concentrated in vacuo. The resulting crude product was chromatographed on silica gel 60 to give compound 4(a).

(b)
9,11-Dideoxy-13,14-dihydro-2',9α-methano-3-oxa-11-oxo-15-(4'-tetrahydropyranyl)-1,4,5,6,16,17,18,19,20-nonanor-3,7-(1',3'-interphenylene)-12-epi-$PGF_1$,15-tetrahydropyranyl ether To a solution of 4.95 g of the compound of Example 4(a) in 250 ml of degassed absolute ethanol was added a solution of 1.67 g (1.56 g/atom) of 10% palladium on carbon and 112 mg (0.81 mmol) of anhydrous potassium carbonate. The resulting mixture was hydrogenated at 50 psi (3.4 atm) for 42 hours after which the mixture was filtered through a pad of 1:1 celite/anhydrous magnesium sulfate (30 g). The filter cake was washed with two 200 ml portions of ethyl acetate. The colorless solution was concentrated in vacuo using 200 ml of toluene to azeotrope the last traces of water and ethanol to give 5.2 g of colorless oil. The colorless oil was dissolved in 65 ml of acetone then degassed and flushed with nitrogen and cooled to −40° to −35° C. The solution was treated dropwise with 4.78 ml (12.8 mmol) of Jones Reagent over 10 to 15 minutes and stirred at −40° to −35° for 2 hours under nitrogen. The excess Jones Reagent was quenched with 3.1 ml (40 mmol) of 2-propanol at −40° to −35° and the mixture was stirred for 30 minutes after which 3 g of solid sodium bicarbonate was added. The mixture was stirred for 15 minutes at ambient temperature after which the greeen suspension was filtered through celite and the filter cake was washed with four 70 ml portions of ethyl acetate. The combined filtrates were washed with two 100 ml portions of saturated aqueous sodium bicarbonate and 100 ml of brine. The aqueous washes were combined and back extracted with 100 ml of ethyl acetate. The organic layers were combined, dried over anhydrous sodium sulfate, filtered, and concentrated in vacuo. The resulting dark brown oil was filtered through 20 g of silica gel 60 compound 4(b).

(c)
9,11-Dideoxy-13,14-dihydro-2',9α-methano-3-oxa-11-oxo15-(4'-tetrahydropyranyl)-1,4,5,6,16,17,18,19,20-nonanor-3,7-(1',3'-interphenylene)$PGF_1$,15-(tetrahydropyranyl ether)

To 4.7 g of the compound of Example 4(b) in 450 ml of 95% ethanol was added 90 ml of 10% aqueous sodium hydroxide and the resulting solution was degassed and flushed with nitrogen and heated at reflux (bath temperature 105°) for 7.5 hours under nitrogen. The reaction was cooled to room temperature and approximately two-thirds of the solvent was removed in vacuo at room temperature and the remaining material was diluted with 500 ml of brine and extracted with three 200 ml portions of ethyl acetate. The combined organics were washed with 200 ml of brine, dried over anhydrous sodium sulfate, filtered and concentrated in vacuo. The crude product was flash chromatographed on silica gel to give the title compound 4(c).

(d)
9-Deoxy-13,14-dihydro-2',9α-methano-3-oxa-15-(4'-tetrahydropyranyl)-1,4,5,6,16,17,18,19,20-nonanor-3,7-(1',3'-interphenylene)-$PGF_1$ To 2.80 g of sodium borohydride, degassed and flushed with nitrogen, and cooled to −30°, was slowly added 350 ml of absolute methanol and the resulting material was stirred for 10 minutes and treated with a solution of 10.2 g of the compound of Example 4(c) in 15 ml of dry methylene chloride and 76 ml of absolute methanol dropwise maintaining the temperature of the solution at −30°. The resulting solution was stirred at −30° for 4 hours, then at −25° for 2.5 hours after which the reaction was quenched with 19.0 ml of glacial acetic acid then diluted with 600 ml of brine and extracted with four 250 ml portions of ethyl acetate. The organic layers were combined and washed with 300 ml of saturated aqueous sodium bicarbonate, then washed with 300 ml of brine, dried over anhydrous sodium sulfate, filtered and concentrated in vacuo to give 10.1 g of a colorless oil. The oil was dissolved in 60 ml of tetrahydrofuran and diluted with 180 ml of glacial acetic acid and 90 ml of deionized water, degassed and flushed with nitrogen, and stirred at 40° to 45° under nitrogen for 3 hours. The solution was then cooled to room temperature, diluted with 500 ml of brine and extracted with three 250 ml portions of 3:2 ethyl acetate/hexane. The organic layers were combined and washed with four 300 ml portions of brine. The aqueous layers were combined and back extracted with two 250 ml portions of 3:2 ethyl acetate/hexane. All the organic layers were combined, dried over anhydrous sodium sulfate, filtered and concentrated in vacuo using two 300 ml portions of toluene to azeotrope the acetic acid. The resulting colorless oil was chromatographed on 700 g of silica gel 60 to give the title compound 4(d).

(e) A solution of 250 ml of dry tetrahydrofuran and 8.3 ml (47.7 mmol) of diphenylphosphine, degassed and cooled to 0° to 5° C. under nitrogen, was treated with 30.0 ml (46.5 mmol) of n-butyllithium (1.55M in hexane) dropwise over 15 minutes then stirred an additional 30 minutes at ambient temperature after which 5.6 g of the compound of Example 4(d) in 50 ml of dry tetrahydrofuran was added under nitrogen pressure over 15 minutes. An additional two 10 ml portions of tetrahydrofuran were added and the mixture was heated at reflux for 8 hours under nitrogen. The solution was cooled to 0° to 5° C. after which 11.0 ml (63.6 mmol) of diphenylphosphine was added, then treated with 41.0 ml (63.6 mmol) of n-butyllithium (1.55M in hexane) dropwise over 10 to 15 minutes. The solution was stirred at ambient temperature for 30 minutes then refluxed for 16 hours all under nitrogen pressure. The solution was then cooled to 0° to 5° C. and poured into 465 ml of ice cold brine containing 125 ml of 1N aqueous hydrochloric acid (pH 3–4) and extracted with three 200 ml portions of ethyl acetate. The organic layers were combined, washed with 200 ml of brine, dried over anhydrous sodium sulfate, filtered, and concentrated in vacuo. The resulting colorless oil was chromatographed on 400 g of silica gel 60 and the product was combined with 22.8 g (165 mmol) of anhydrous potassium carbonate, and 17.8 ml (281 mmol) of chloroacetylnitrile and 150 ml of acetone. The solution was degassed and flushed with nitrogen and refluxed for 24 hours under nitrogen and cooled to 15° to 20° C., diluted with 200 ml of 1:1 brine/water and extracted with 600 ml of ethyl acetate. The organic layer was washed with 200 ml of brine. The aqueous layers were combined and extracted with 200 ml of ethyl acetate. The organic layers were combined, dried over anhydrous sodium sulfate, filtered and concentrated in vacuo. The resulting black oil was chromatographed on 400 g of silica gel 60 and the product was combined with 100 ml (445 mmol) of 25% aqueous potassium hydroxide, degassed and flushed with nitrogen. The solution was refluxed for 6 hours, cooled to 0° to 5°, acidified to pH 6 with 400 ml of ice cold 1N aqueous hydrochloric acid in 1 L of brine, and extracted with four 300 ml portions of ethyl acetate. The combined organic layers were washed with 500 ml of brine, dried over anhydrous sodium sulfate, filtered, and concentrated in vacuo. The resulting pink to red solid was chromatographed on 400 g of CC-4 acid washed silica gel to give 9-deoxy-13,14-dihydro-2',9α-methano-3-oxa-15-(4'-tetrahydropyranyl)-4,5,16,17,18,19,20-octanor-(1',3'-interphenylene)-PGF$_1$.

EXAMPLE 5

15-Cyclohexyl-9,15-dideoxy-13,14-dihydro-2',9α-methano-3-oxa-4,5,6,16,17,18,19,20-octanor-3,7-(1',3'-interphenylene)PGF$_1$ (Formula Q is COOH; Z$_4$ is —CH$_2$—; L$_{60}$ is H; L$_{20}$ is α-OH,β-H; Y$_1$ is CH$_2$CH$_2$;

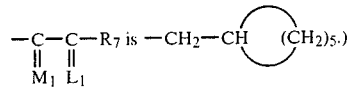

(a) 1-Bromo-4-cyclohexylbutane

4-Cyclohexyl-butan-1-ol(8.1 ml, 47 mmol) at −5° C. under nitrogen was treated dropwise over 10–15 min with 2.2 ml (23 mmol) of phosphorus tribromide, stirred at 0° C. for 15 min, room temperature for 2 h, then at 100° C. for 1.5 h before cooling to 0° C. The reaction was quenched with 50 g of ice, diluted with 100 ml of brine, and extracted with ether. The combined organics were washed with brine, dried over anhydrous sodium sulfate, filtered, concentrated, and distilled at 2 mm Hg, 100° C., to give 9.84 g (96%) of 1-bromo-4-cyclohexylbutane as a colorless liquid. NMR (CDCl$_3$, TMS) δ 0.6–2.3 (m, 17H), 3.43 (t, J=7 Hz, 2H).

(b) Dimethylbutyl(4-cyclohexyl)phosphonate

A solution of 6.7 ml (52 mmol) of diethylphosphite in 400 ml of dry tetrahydrofuran was degassed, cooled to −75° C. under nitrogen, treated dropwise with 36.4 ml (57 mmol) of 1.57M n-butyllithium in hexane, stirred 30 min at −75° C., 30 min at 0° C., then treated with 9.4 g (43 mmol) of 1-bromo-4-cyclohexylbutane in 50 ml of tetrahydrofuran dropwise over 10 min. The solution was stirred at room temperature for 1 h, then at 60° C. for 4 h, before cooling to 0° C. and quenching with 500 ml of brine containing 40 ml of 1N aqueous hydrochloric acid. The layers were separated and the aqueous layer was extracted with ethyl acetate. The organic layers were combined, washed with brine, dried over anyhydrous sodium sulfate, filtered, concentrated and chromatographed on silica gel eluting with ethyl acetate in hexane to give 9.6 g (81%) of dimethylbutyl(4-cyclohexyl)phosphonate as a colorless oil. NMR (CDCl$_3$, TMS): δ 0.5–1.9 (m, 25H), 4.13 (two q, 4H).

(c) 15-Cyclohexyl-8,12-dehydro-13,14-dihydro-2',9α-methano-3-oxa 11-oxo-1,4,5,6,16,17,18,19,20-nonanor-9,11,15-trideoxy-3,7-(1',3'-interphenylene)-PGF$_1$ A solution of 2.17 g (7.85 mmol) of dimethylbutyl(4-cyclohexyl)phosphonate in 150 ml of dry tetrahydrofuran was degassed, cooled to −75° C. under nitrogen, treated dropwise with 5.0 ml (8.0 mmol) of 1.60 M n-butyllithium in hexane, stirred at −75° C. for 1 h, treated with 0.80 g (3.7 mmol) of 2,3,3A,4-tetrahydro-5-methoxy-2-oxo-naphtho[2,3-b]furan in 20 ml of dry tetrahydrofuran, stirred at −75° C. for 1 h, then 2 h while warming to −40° C., and 15 min at ambient temperature. The reaction was cooled to 0° C., treated with 0.21 ml (3.6 mmol) of glacial acetic acid, stirred at room temperature for 15 min, then at 55°–60° C. for 6 h, cooled to 0° C., and quenched with 250 ml of brine containing 6 ml of 1N aqueous hydrochloric acid. The layers were separated and the aqueous layer was extracted with ethyl acetate. The combined organic layers were washed with 3:1 brine/saturated aqueous sodium bicarbonate, then with brine, dried over anhydrous sodium sulfate, filtered, concentrated in vacuo, and chromatographed on silica gel eluting with ethyl acetate in hexane to give 0.855 g (68%) of 15-Cyclohexyl-8,12-dehydro-13,14-dihydro-2',9α-methano-3-oxa-11-oxo-1,4,5,6,16,17,18,19,20-nonanor-9,11,15-trideoxy-3,7-(1',3'-interphenylene)-PGF$_1$.

NMR (CDCl$_3$, TMS) δ 0.6–3.1 (m, 21H), 3.4–4.1 (m including 3H singled at 3.87, 6H), 6.6–7.3 (m, 3H).

Infrared (film): 1700, 1655, 1595, 1475, 1410, 1370, 1315, 1270, 1255, 1090, 1080, 765 cm$^{-1}$.

TLC (silica gel GF): R$_f$ 0.40 in 20% ethyl acetate in hexane.

(d)

15-Cyclohexyl-13,14-dihydro-2',9α-methano-3-oxa-11-oxa-1,4,5,6,16,17,18,19,20-nonanor-9,11,15-trideoxy-3,7-(1',3'-interphenylene)-PGF$_1$ A suspension of 1.37 g (4.05 mmole) of the compound from 5(c), 490 mg of 10% palladium on carbon, and 50 mg (0.36 mmol) of anhydrous potassium carbonate in 75 ml of absolute ethanol was hydrogenated at 3 atm (50 lb/sq in) for 46 hours and then filtered through celite, washing the filter cake with ethyl acetate. The solvents were combined, concentrated in vacuo and chromatographed on silica gel eluting with ethyl acetate in hexane to give 1.10 g (80%) of a 3:1 mixture of the title compound with the corresponding 12-α analog as a colorless oil.

Physical properties for the title compound:

NMR (CDCl$_3$, TMS): δ 0.6–3.3 (m, 26H), 4.83 (s, 3H), 6.6–7.3 (m, 3H)

Infrared: γmax (film): 1740, 1595, 1480, 1450, 1270, 1100, 1055, 975, 885, 780 cm$^{-1}$.

TLC (Silica Gel GF): 20% ethyl acetate in hexane (e)

15-Cyclohexyl-9,15-dideoxy-13,14-dihydro-2',9α-methano-3-oxa-1,4,5,6,16,17,18,19,20-nonanor-3,7-(1',3'-interphenylene)-PGF$_1$ A solution of 400 mg (1.17 mmol) of the mixture of the compound 5(d) with the corresponding 12α-analog was dissolved in 40 ml of absolute ethanol and 4 ml of dry methylene chloride, degassed, cooled to −10° under nitrogen, treated with 8 ml of ice cold 10% aqueous sodium hydroxide, stirred 15 min, and then treated with 60 mg (1.59 mmol) of sodium borohydride. At 1.0 h, 2.0 h and 6.0 h an additional 60 mg (1.59 mmol) of sodium borohydride was added to the reaction mixture for a total of 240 mg (6.34 mmol) of sodium borohydride. The mixture was stirred for 2.0 hour at −10° C. after the last addition, carefully quenched at −10° C. with 2.9 ml of glacial acetic acid, diluted with 250 ml of brine, and extracted with ethyl acetate. The organic layers were combined, washed with saturated aqueous sodium bicarbonate and with brine, dried over anhydrous sodium sulfate, filtered, concentrated in vacuo, and chromatographed on Silica Gel eluting with ethyl acetate in hexane to give 373 mg (93%) of the title compound as a white oily solid.

NMR (CDCl$_3$, TMS): δ 0.6–2.9 (m, 28H), 3.83 (s, 3H), 6.6–7.3 (m, 3H).

Infrared γmax (film): 3350, 1595, 1480, 1455, 1265, 1105, 770, 730 cm$^{-1}$.

TLC (Silica Gel GF): Rf=0.29 in 20% ethyl acetate in hexane.

(f)

15-Cyclohexyl-9,15-dideoxy-13,14-dihydro-2',9α-methanol-3-oxa-1,2,4,6,16,17,18,19,20-decanor-3,7-(1',3'-interphenylene)-PGF$_1$ A solution of 0.9 ml (5 mmol) of diphenylphosphine in 30 ml of dry tetrahydrofuran under nitrogen at 0° C. was treated with 3.2 ml (5.1 mmol) of 1.6M n-butyllithium in hexane, stirred for 30 minutes at room temperature, then treated with 557 mg (1.6 mmol) of the compound from 5(e) in 10 ml of dry tetrahydrofuran, and heated at 70° C. for 7 hours. The orange solution was cooled to 0° C., treated with 0.9 ml (5 mmol) of diphenylphosphine and 3.2 ml (5.1 mmol) of 1.6M n-butyllithium in hexane, stirred at room temperature for 30 minutes, then at 70° C. for 18 hours, before cooling to 0° C., diluting with 100 ml of brine containing 10 ml of 1N aqueous hydrochloric acid, and extracting with ethyl acetate. The combined organics were washed with brine, dried over anhydrous sodium sulfate, filtered, concentrated, and chromatographed on Silica Gel eluting with acetone in methylene chloride to give 509 mg (95%) of the title compound as a white foam.

NMR (CDCl$_3$, TMS): δ 0.5–2.9 (m, 28H), 3.4–3.9 (m, 1H), 6.5–7.2 (m, 3H).

Infrared γmax (mull): 3430, 3160, 1600, 1465, 1375, 1285, 1260, 1095, 775, 745 cm$^{-1}$.

TLC (Silica Gel GF): Rf=0.24 in 5% acetone in methylene chloride.

(g)

2-Cyano-5-cyclohexyl-2-decarboxy-9,15-dideoxy-13,14-dihydro-2',9α-methano-3-oxa-4,5,6,16,17,18,19,20-octanor-3,7-(1',3'-interphenylene)-PGF$_1$ A suspension of 450 mg (1.37 mmol) of the compound from 5(f), 1.8 ml (28 mmol) of chroroacetonitrile, and 2.2 g (16 mmol) of anhydrous potassium carbonate in 20 ml of acetone was degassed, heated at 65° C. for 24 hours under nitrogen, cooled, diluted with 100 ml of brine, and extracted with ethyl acetate. The combined organics were washed with brine, dried over anhydrous sodium sulfate, filtered, concentrated, and chromatographed on Silica Gel eluting with ethyl acetate in hexane to give 498 mg (99%) of the title compound as a colorless oil which solidified in the refrigerator.

NMR (CDCl$_3$, TMS): δ0.6–3.0 (m, 27H), 3.5–3.9 (m, 1H), 4.74 (s, 2H), 6.7–7.3 (m, 3H).

Infrared γmax (film): 3400, 2350(w), 1595, 1465, 1450, 1240, 1105, 890, 770 cm$^{-1}$.

TLC (Silica Gel GF): Rf=0.33 in 30% ethyl acetate in hexane.

(h)

15-cyclohexyl-9,15-dideoxy-13,14-dihydro-2',9α-methano-3-oxa-4,5,6,16,17,18,19,20-octanor-3,7-(1',3'-interphenylene)-PGF$_1$ A solution of 450 mg (1.22 mmol) of the compound from 5(g) in 30 ml of methanol was treated with 10 ml of 25% aqueous potassium hydroxide, degassed, heated at 90° C. under nitrogen for 5 hours, cooled to 0° C., acidified to pH 5–6 with 1N aqueous hydrochloric acid, diluted with 20 ml brine, and extracted with ethyl acetate. The combined organic layers were washed with brine, dried over anhydrous sodium sulfate, filtered, concentrated, and chromatographed on CC-4 acid washed silica gel eluting with ethyl acetate in hexane to give 461 mg (98%) of solid which was crystallized from hot tetrahydrofuran/hexane to give 305 mg of the title compound as a white solid, mp 158°–160° C.

NMR (Acetone-d$_6$, TMS): δ0.6–3.0 (m, 24H), 3.4–4.6 (m, 5H), 4.73 (s, 2H), 6.7–7.3 (m, 3H).

Infrared γmax (film): 3420, 1735, 1590, 1460, 1235, 1120, 1080, 1015, 785, 720 cm$^{-1}$.

TLC (Silica Gel GF): Rf=0.57 in the organic phase of 9:2:5:10 ethyl acetate/acetic acid/cyclohexane/water (Rf=0.15 for 6β-PGI$_2$ in the same system).

EXAMPLE 6

15-Cyclohexyl-9,15-dideoxy-13,14-dihydro-16-(RS)-hydroxy-2',9α-methano-3-oxa-4,5,6,16,17,18,19,20-octanor-3,7-(1',3'-interphenylene)-PGF$_1$ (a) 4-Cyclohexylidene butanoic acid, methyl ester A twice hexane washed suspension of 15.0 g (312 mmol) sodium hydride (50% in mineral oil) in 600 ml of dry dimethyl sulfoxide was heated under nitrogen at 60° C. for 1.5 hour, cooled to 15° C., and treated portionwise over 15 min with 60 g (140 mmol) of 3-carboxypropyl triphenylphosphonium bromide. The bright red solution was stirred at room temperature for 1 hour, then treated with 9.6 ml (93 mmol) of cyclohexanone in 100 ml of dry tetrahydrofuran, stirred 1 hour at room temperature, 2 hours at 40°–45° C., cooled to 0° C., quenched with 10 ml of water, diluted with 600 ml of ice water containing 50 ml of concentrated sulfuric acid and 250 ml of brine, and extracted with ethyl acetate. The combined organic layers were washed with brine, dried over anhydrous sodium sulfate, filtered, and concentrated in vacuo. The resulting yellow oil was dissolved in 500 ml of acetonitrile, degassed, treated with 25 ml (143 mmol) of diisopropylethylamine and 50 ml (792 mmol) of methyliodide, stirred for 18 hours under nitrogen at room temperature, diluted with 250 ml of ethyl acetate, washed with 5% sodium sulfate and with saturated aqueous sodium bicarbonate. The organic layers were washed with brine, dried over anhydrous sodium sulfate, filtered, concentrated in vacuo, and chromatographed on Silica Gel eluting with ethyl acetate in hexane to give 11.43 g (68%) of the title compound as a pale yellow oil.

(b) 4-Cyclohexylidenebutan-1-ol

A suspension of 5.8 g (150 mmol) of lithium aluminum hydride in 300 ml of dry tetrahydrofuran at 0° C. under nitrogen was treated with 13.8 g (76 mmol) of ester from 6(a) in 50 ml of dry tetrahydrofuran, stirred 30 min at 0° C., 2 hours at room temperature, cooled to 0° C., quenched with 5.8 ml water and 5.8 ml of 15% aqueous sodium hydroxide and 17.4 ml of water, stirred 30 min at room temperature, dried over anhydrous magnesium sulfate, filtered, concentrated in vacuo, and chromatographed on Silica Gel to give 10.5 g (90%) of title compound 6(b) as a colorless oil.

(c) 4-Cyclohexylidene-1-iodobutane

A solution of 9.6 g (62.2 mmol) of title compound 6(b) in 500 ml of dry methylene chloride was treated with 13.8 ml (100 ml) of triethylamine, degassed, cooled to 0° under nitrogen, treated dropwise with 7.0 ml (90 mmol) of methane sulfonyl chloride, stirred 30 min at 0° C., 3 hours at room temperature, and poured onto 500 g of ice stirring until the ice melted. The layers were separated, the aqueous layer was extracted with methylene chloride, the organic layers combined, washed with brine, dried over anhydrous magnesium sulfate, filered, and concentrated in vacuo to a yellow oil [TLC (Silica Gel GF): Rf=0.26 in hexane].

The yellow oil was dissolved in 400 ml of acetone, degassed with nitrogen, treated with 20 g (133 mmol) of sodium iodide, heated at 65° C. for 2.5 hours under nitrogen, cooled to 0° C., removed most of the acetone in vacuo at room temperature, diluted with ethyl acetate which was washed with 5% sodium thiosulfate, brine, dried over anhydrous sodium sulfate, filtered, concentrated in vacuo, and chromatographed on Silica Gel eluting with hexane to give 15.84 g (96%) of title compound 6(c) as a colorless oil.

(d) Dimethyl-(4-cyclohexylidene-1-butyl)phosphonate

A solution of 9.1 ml (70 mmol) of diethyl phosphite in 400 ml of dry tetrahydrofuran was degassed, cooled to −75° C. under nitrogen, treated dropwise with 50.0 ml (77 mmol) of 1.55M n-butyllithium in hexane, stirred 30 min at −75° C., 30 min at 0° C., treated with 15.5 g (59 mol) of title compound 6(c) in 50 ml of tetrahydrofuran, stirred at room temperature for 1 hour, 70° C. for 4 hour, cooled to 0° C., diluted with 500 ml of brine containing 40 ml of 1N aqueous hydrochloric acid, separated layers, and extracted the aqueous alyer with ethyl acetate. The combined organic layers were washed with brine, dried over anhydrous sodium sulfate, filtered, concentrated in vacuo, and chromatographed on Silica Gel eluting with ethyl acetate in hexane to give 13.03 g (80%) of title compound 6(d) as a colorless oil.

(e) 15-Cyclohexyl-13,14-dihydro-2',9α-methano-3-oxo-1,4,5,6,16,17,18,19,20-nonanor-8,12,15,16-tetrahydro-9,11,15-trideoxy-3,7-(1',3'-interphenylene)-PGE$_1$ A solution of 5.33 g (19.42 mmol) of the compound from 6(d) in 250 ml of dry tetrahydrofuran was degassed, cooled to −75° C. under nitrogen, treated dropwise with 12.7 ml (20.4 mml) of 1.60M n-butyllithium in hexane, stirred at −75° C. for 1 hour, treated with 2.0 g (9.25 mmol) of 2,3,3A,4-tetrahydro-5-methoxy-2-oxonaphtho[2,3-b]-furan in 40 ml of dry tetrahydrofuran, stirred at −75° C. for 1 hour, then 2 hours while warming to −40° C., and 15 minutes at ambient temperature. The reaction was cooled to 0° C., treated with 0.55 ml (9.71 mmol) of glacial acetic acid, stirred at room temperature for 15 minutes, then at 55°–60° C. for 6 hours, cooled to 0° C., and quenced with 250 ml of brine containing 10 ml of 1N aqueous hydrochloric acid. The layers were separated, and the aqueous layer was extracted with ethyl acetate. The combined organic layers were washed with 3:1 brine/saturated aqueous sodium bicarbonate, then with brine, dried over anhydrous sodium sulfate, filtered, concentrated in vacuo, and chromatographed on Silica Gel eluting with ethyl acetate in hexane to give 1.78 g (78%) of title compound 6(e) as a white solid.

NMR (CDCl$_3$, TMS): δ1.1–3.0 (m, 18H), 3.2–4.0 (m, includng 3H singlet at 3.83, 6H), 5.06 (t, J=9 Hz, 1H), 6.6–7.3 (m, 3H).

Infrared γmax (film): 2930, 1655, 1600, 1590, 1475, 1460, 1450, 1275, 1255, 1095, 1075, 780 cm$^{-1}$.

TLC (Silica Gel GF): Rf=0.41 in 20% ethyl acetate in hexane.

(f)
15-Cyclohexyl-8,12-didehydro-13,14-dihydro-15,16-epoxy-2',9α-methano-3-oxa-11-oxo-1,4,5,6,16,17,18,19,20-nonanor-9,11,15-trideoxy-3,7-(1',3'-interphenylene)-PGE$_1$ A solution of 1.53 g (4.54 mmol) of title compound 6(e) in 60 ml of dry methylene chloride was degassed, cooled to 0° C. under nitrogen, treated with 1.02 g (5.9 mml) of m-chloroperoxybenzoic acid in one portion, stirred at 0° C. for 2 hours, quenched with 100 ml of 10% aqueous sodium sulfite, and extracted with methylene chloride. The organics were combined, washed with 10% aqueous sodium sulfate, then with saturated aqueous sodium bicarbonate, then with brine, dried over anhydrous sodium sulfate, filtered, concentrated in vacuo, and chromatographed on Silica Gel eluting with ethyl acetate in hexane to give 1.56 g (98%) of title compound 6(f) as a white solid, mp 91°–95° C.

NMR (CDCl$_3$, TMS): δ1.1–3.1 (m, 1H), 3.4–4.1 (m, including 3H) singlet at 3.84, 6H), 6.7–7.3 (m, 3H).

Infrared γmax (film): 2950, 1700, 1660, 1595, 1470, 1445, 1370, 1315, 1275, 1255, 1090, 1080, 900, 770, 705 cm$^{-1}$.

TLC (Silica Gel GF): Rf=0.18 in 20% ethyl acetate in hexane.

(g)
15-Cyclohexyl-13,14-dihydro-15,16-epoxy-2',9α-methano-3-oxa-11-oxo-1,4,5,6,16,17,18,19,20-nonanor-9,11,15-trideoxy-3,7-(1',3'-interphenylene)-PGF$_1$ A suspension of 1.4 g (3.97 mmol) of the compound from 5(f), 800 mg of 10% palladium on carbon, and 40 mg of anhydrous potassium carbonate in 120 ml of absolute ethanol was hydrogenated at 50 lb/sq in (~3.4 atm) 48 hours, filtered through a pad of ceite which was washed with ethyl acetate, concentrated in vacuo, and chromatographed on Silica Gel eluting with ethyl acetate in hexane to give 660 mg (47%) of the title compound.

NMR (CDCl$_3$, TMS): δ1.3–3.4 (m, 24H), 3.83 (s, 3H), 6.7–7.3 (m, 3H).

Infrared γmax (film): 1740, 1695, 1470, 1445, 1265, 1255, 1090, 900, 765 cm$^{-1}$.

TLC (Silica Gel GF): R$_f$=0.27 in 20% ethyl acetate in hexane.

(h)
15-Cyclohexyl-9,15-dideoxy-13,14-dihydro-15,16-epoxy-2',9α-methano-3-oxa-1,4,5,6,16,17,18,19,20-nonanor-3,7-(1',3'-interphenylene)-PGF$_1$ A solution of 230 mg (6.2 mmol) of sodium borohydride in 30 ml of anhydrous methanol at −20° C. under nitrogen was treated dropwise with 620 mg (1.7 mmol) of compound 6(g) in 1.5 ml of methylene chloride and 7.5 ml of methanol, stirred at −20° C. for 1 hour, quenched with 2 ml of glacial acetic acid, diluted with 100 ml of brine, and extracted with ethyl acetate. The combined organics were washed with brine, dried over anhydrous sodium sulfate, filtered, concentrated in vacuo, and chromatographed on silica Gel eluting with 25% ethyl acetate in hexane to give 350 mg of title compound 6(h).

NMR (CDCl$_3$, TMS): δ1.0–3.2 (m, 23H), 3.5–4.1 (m, including 3H singlet at 3.77, 4H), 6.6–7.3 (m, 3H).

Infrared γmax (film): 3450, 1595, 1475, 1455, 1265, 1105, 1075, 1030, 900, 700 cm$^{-1}$.

TLC (Silica Gel GF): Rf=0.24 in 30% ethyl acetate in hexane).

(i)
15-Cyclohexyl-9,15-dideoxy-13,14-dihydro-16-(RS)hydroxy-2',9α-methano-3-oa-1,4,5,6,16,17,18,19,20-nonanor-3,7-(1',3'-interphenylene)-PGF$_1$ A solution of 460 mg (1.3 mmol) of compound 6(h) in 15 ml of dry tetrahydrofuran was degassed, cooled to 0° C. under nitrogen, treated in one portion with 75 mg (2.0 mmol) of lithium aluminum hydride, stirred 30 min at 0° C., 4 hours at room temperature, cooled to 0° C., quenched with the successive additions of 1 ml of water, 1 ml of 15% aqueous sodium hydroxide, and 3 ml of water, dried over anhydrous sodium sulfate, filtered, concentrated in vacuo, and chromatographed on Silica Gel eluting with 40% ethyl acetate in hexane with 1% triethylamine to give 350 mg of title compound 6(i) as a white solid, mp 153°–154° C.

NMR (CDCl$_3$/Acetone-d$_6$, TMS): δ0.9–3.0 (m, 27H), 3.5–3.8 (m, including 3H singlet at 3.83, 4H), 6.6–7.3 (m, 3H).

Infrared γmax (film): 3350, 1595, 1465, 1380, 1265, 1105, 1025, 965, 770 cm$^{-1}$.

TLC (Silica Gel Gf): Rf=0.27 in 40% ethyl acetate in hexane with 1% triethylamine.

(j)
2-Cyano-15-cyclohexyl-2-decarboxy-9,15-dideoxy-13,14-dihydro-16-(RS)hydroxy-2',9α-methano-3-oxa-4,5,6,16,17,18,19,20-octanor-3,7-(1',3'-interphenylene)-PGF$_1$ A solution of 0.45 ml (2.5 mmol) of diphenylphosphine in 15 ml of dry tetrahydrofuran under nitrogen at 0° C. was treated with 1.6 ml (2.6 mmol) of 1.6M n-butyllithium in hexane stirred for 30 minutes at room temperature, then treated with 330 mg (0.92 mmol) in compound 6(i) in 5 ml of dry tetrahydrofuran, and heated at 70° C. for 7 hours. The orange solution was cooled to 0° C., treated with 0.45 ml (2.5 mmol) of diphenylphosphine and 1.6 ml (2.6 mmol) of 1.6M n-butyllithium in hexane, stirred at room temperature for 30 minutes, then at 70° C. for 18 hours, before cooling to 0° C., diluting with 100 ml of brine, containing 20 ml of 1N aqueous hydrochloric acid, and extracting with ethyl acetate. The combined organics were washed with brine, dried over anhydrous sodium sulfate, filtered, concentrated in vacuo, and chromatographed on Silica Gel eluting with 30% acetone in methylene chloride with 1% triethylamine to give 350 mg of 15-cyclohexyl-9,15-dideoxy-13,14-dihydro-16(RS)hydroxy-2',9α-methano-3-oxa-1,2,4,6,16,17,18,19,20-decanor-3,7-(1',3'-interphenylene)-PGF$_1$.

NMR (CDCl$_3$, TMS): δ0.6–4.0 (m, 30H), 6.6–7.

TLC (Silica Gel GF): Rf=0.22 in 60% ethyl acetate in hexane with 1% triethylamine.

A suspension of 300 mg (0.87 mmol) of the above obtained interphenylene PGF$_1$, 0.5 ml (8 mmol) of chloroacetonitrile, and 1.0 g (7.2 mmol) of anhydrous potassium carbonate in 15 ml of acetone was degassed, heated at 65° C. for 24 hours under nitrogen, cooled, diluted with 100 ml of brine, and extracted with ethyl acetate. The combined organics were washed with brine, dried over anhydrous sodium sulfate, filtered, concentrated, and chromatographed on Silica Gel eluting with 60% ethyl acetate in hexane to give 256 mg (72%) of title compound 6(j) as a colorless oil which solidified in the refrigerator, mp 90°-92° C.

NMR (CDCl$_3$, TMS): δ0.9-3.1 (m, 26H), 3.4-3.9 (m, 2H), 4.97 (s, 2H), 6.7-7.3 (m, 3H).

Infrared γmax (mull): 3400, 3260, 1590, 1460, 1380, 1275, 1240, 1100, 1070, 960, 770, 725 cm$^{-1}$.

TLC (Silica Gel GF): Rf=0.56 In 30% acetone in methylene chloride with 1% triethylamine.

(k)

15-Cyclohexyl-9,15-dideoxy-13,14-dihydro-16-(RS)-hydroxy-2',9α-methano-3-oxa-4,5,6,16,17,18,19,20-octanor-3,7-(1',3'-interphenylene)-PGF$_1$ A solution of 225 mg (0.59 mmol) of compound 5(j) in 20 ml of methanol was treated with 7 ml of 25% aqueous potassium hydroxide, degassed, heated at 90° C. under nitrogen for 5 hours, cooled to 0° C., acidified to pH 5-6 with 1N aqueous hydrochloric acid, diluted with 200 ml brine, and extracted with ethyl acetate. The combined organic layers were washed with brine, dried over anhydrous sodium sulfate, filtered, concentrated, triturated with ether and hexane at room temperature, and allowed to stand overnight under nitrogen to give after filtration 200 mg (84% of title compound 5(k) as white crystals, mp 154°-156° C.

NMR (CDCl$_3$/Acetone-d$_6$, TMS): δ0.6-4.0 (m, 29H), 4.67 (s, 2H), 6.6-7.3 (m, 3H).

Infrared γmax (mull): 3500, 3250, 1740, 1590, 1465, 1225, 1120, 970, 770, 745 cm$^{-1}$.

TLC (Silica Gel GF): Rf=0.41 in the organic phase of 9:2:5:10 ethyl acetate/acetic acid/cyclohexane/water. Rf=0.20 for 6β-PGI$_2$ in the same system).

EXAMPLE 7

15-Phenyl-9,15-dideoxy-13,14-dihydro-2',9α-methano-3-oxa-4,5,6,16,17,18,19,20-octanor-3,7-(1',3'-interphenylene)-PGF$_1$ (Formula I: Q is COOH; Z$_4$ is CH$_2$; L$_{60}$ is H; L$_{20}$ is α:OH; β-H; Y$_1$ is CH$_2$CH$_2$; and

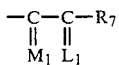

is benzyl).

(a) 4-Phenyl-1-bromobutane

A solution of 7.0 g (47 mmol) of 4-phenyl-1-butanol (10) in 200 ml of methylene chloride at 0° C. under a nitrogen atmosphere was treated with 11 ml of triethylamine, then with 5.6 ml of methanesulfonyl chloride, stirred 30 min at 0° C. and then 1 hour at room temperature, poured onto ice, and the layers were separated. The aqueous layer was washed with additional methylene chloride, and the combined organics washed with saturated aqueous sodium bicarbonate and then with brine and dried (Na$_2$SO$_4$). The solvents were removed in vacuo to give the corresponding mesylate of 10 which was dissolved in 200 ml of dry tetrahydrofuran and treated with 23.6 g of tetra-n-butyl ammonium bromide. After 48 hours at room temperature the resulting solution was diluted with aqueous sodium bicarbonate and extracted with hexane and dried (Na$_2$SO$_4$). The solvents were removed in vacuo and the residue distilled to afford 4-phenyl-1-bromobutane.

(b) Dimethylbutyl(4-phenyl)phosphonate

A solution of 6.7 ml of diethylphosphite in 400 ml of dry tetrahydrofuran was degassed, cooled to −75° C. under nitrogen, treated dropwise with 36.4 ml of 1.57M n-butyllithium in hexane, stirred 30 min at −75° C., 30 min at 0° C., then treated with 9.4 g of 4-phenyl-1-bromobutane in 50 ml of tetrahydrofuran dropwise over 10 min. The solution was stirred at room temperature for 1 hour, then at 60° C. for 4 hour, before cooling to 0° C. and quenching with 500 ml of brine containing 40 ml of 1N aqueous hydrochloric acid. The layers were separated and the aqueous layer was extracted with ethyl acetate. The organic layers were combined, washed with brine, dried over anhydrous sodium sulfate, filtered, concentrated and chromatographed on silica gel to give title compound 7(b).

(c)

15-Phenyl-8,12-dehydro-13,14-dihydro-2',9α-methano-3-oxo-1,4,5,6,16,17,18,19,20-nonanor-9,11,15-trideoxy-3,7-(1',3'-interphenylene)-PGF$_1$ A solution of 4.02 g of compound 7(b) in 250 ml of dry tetrahydrofuran was degassed, cooled to −75° C. under nitrogen, treated dropwise with 9.6 ml of 1.60M n-butyllithium in hexane, stirred at −75° C. for 1 hour, treated with 1.5 g of 2,3,3A,4-tetrahydro-5-methoxy-2-oxo-naphtho[2,3-B]furan in 40 ml of dry tetrahydrofuran. Stirred at −75° C. for 1 hour, then 2 hours while warming to −40° C., and 15 minutes at ambient temperature. The reaction was cooled to 0° C., treated with 0.42 ml of glacial acetic acid, stirred at room temperature for 15 minutes, then at 55°-60° for 6 hours, cooled to 0° C., and quenched with 250 ml of brine containing 9 ml of 1N aqueous hydrochloric acid. The layers were separated and the aqueous layer was extracted with ethyl acetate. The combined organic layers were washed with 3:1 brine/saturated aqueous sodium bicarbonate, then with brine, dried over anhydrous sodium sulfate, filtered, concentrated in vacuo, and chromatographed on silica gel 60 to give title compound 5(c).

(d)

15-Phenyl-13,14-dihydro-2',9α-methano-3-oxa-11-1,4,5,6,16,17,18,19,20-nonanor-9,11,15-trideoxy-3,7-(1',3'-interphenylene)-PGF$_1$ A suspension of 1.37 g of compound 7(c), 490 mg of 10% palladium on carbon, and 50 mg (0.36 mmol) of anhydrous potassium carbonate in 75 ml of absolute ethanol was hydrogenated at 3 atm (50 lb/sq in) for 46 hours and then filtered through celite, washing the filter cake with ethyl acetate. The solvents were combined, concentrated in vacuo and chromatographed on silica gel to give the title compound 7(d) as a colorless oil.

(e)

15-Phenyl-9,15-dideoxy-13,14-dihydro-2',9α-methano-3-oxa-1,4,5,6,16,17,18,19,20-nonanor-3,7-(1',3'-interphenylene)-PGF$_1$ A solution of 285 mg of sodium borohydride in 30 ml of absolute methanol at −20° C. under nitrogen was treated dropwise with a solution of 731 mg of compound 7(d) in 1.5 ml dry methylene chloride and 7.5 ml absolute methanol, stirred for 30 minutes at −20° C., quenched with 0.5 ml glacial acetic acid, diluted with 100 ml of brine, and extracted with ethyl acetate. The combined organics were washed with saturated aqueous sodium bicarbonate and 100 ml of brine, dried over anhydrous sodium sulfate, filtered, concentrated in vacuo, and chromatographed on Silica Gel to give title compound 7(e).

(f)
15-Phenyl-9,15-dideoxy-13,14-dihydro-2',9α-methano-3-oxa-1,2,4,6,16,17,18,19,20-decanor-3,7-(1',3'-interphenylene)-PGF$_1$ A solution of 0.9 ml of diphenylphosphine in 30 ml of dry tetrahydrofuran under nitrogen at 0° C. was treated with 3.2 ml of 1.6M n-butyllithium in hexane, stirred for 30 minutes at room temperature, then treated with 557 mg of compound 7(e) in 10 ml of dry tetrahydrofuran, and heated at 70° C. for 7 hours. The solution was cooled to 0° C., treated with 0.9 ml of diphenylphosphine and 3.2 ml of 1.6M n-butyllithium in hexane, stirred at room temperature for 30 minutes, then at 70° C. for 18 hours, before cooling to 0° C., diluting with 100 ml of brine containing 10 ml of 1N aqueous hydrochloric acid, and extracting with ethyl acetate. The combined organics were washed with brine, dried over anhydrous sodium sulfate, filtered, concentrated, and chromatographed on Silica Gel to give title compound 7(f).

(g)
2-Cyano-15-cyclohexyl-2-decarboxy-9,15-dideoxy-13,14-dihydro-2',9α-methano-3-oxa-4,5,6,16,17,18,19,20-octanor-3,7-(1',3'-interphenylene)-PGF$_1$ A suspension of 450 mg of compound 7(f), 1.8 ml of chloroacetonitrile, and 2.2 g of anhydrous potassium carbonate in 20 ml of acetone, was degassed, heated at 65° C. for 24 hours under nitrogen, cooled, diluted with 100 ml of brine, and extracted with ethyl acetate. The combined organics were washed with brine, dried over anhydrous sodium sulfate, filtered, concentrated, and chromatographed on Silica Gel to give title compound 7(g).

(h)
15-Phenyl-9,15-dideoy-13,14-dihydro-2',9α-methano-3-oxa-4,5,6,16,17,18,19,20-octanor-3,7-(1',3'-interphenylene)-PGF$_1$ A solution of 450 mg of compound 7(g) in 30 ml of methanol was treated with 10 ml of 25% aqueous potassium hydroxide, degassed, heated at 90° C. under nitrogen for 5 hours, cooled to 0° C., acidified to pH 5–6 with 1N aqueous hydrochloric acid, diluted with brine, and extracted with ethyl acetate. The combined organic layers were washed with brine, dried over anhydrous sodium sulfate, filtered, concentrated, and chromatographed on CC-4 acid washed silica gel to give title compound 7(h).

FORMULA CHART

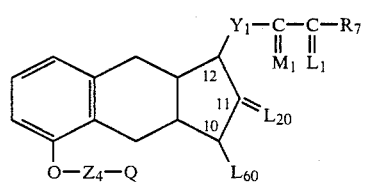

Formula I

FORMULA CHART

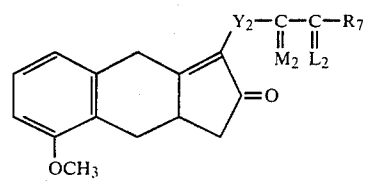

Formula I(a)

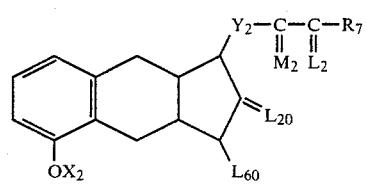

Formula I(b)

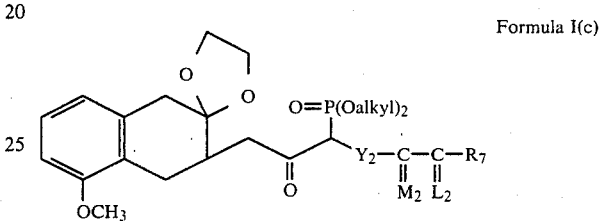

Formula I(c)

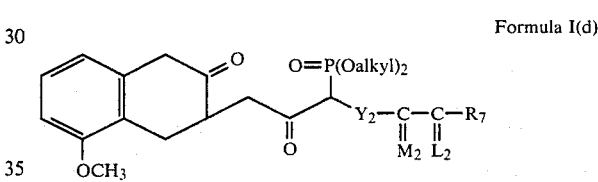

Formula I(d)

CHART A

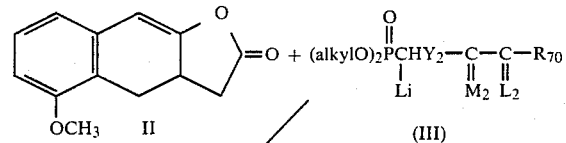

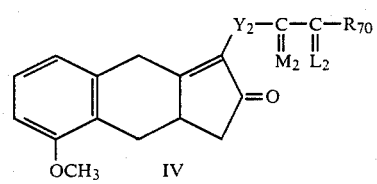

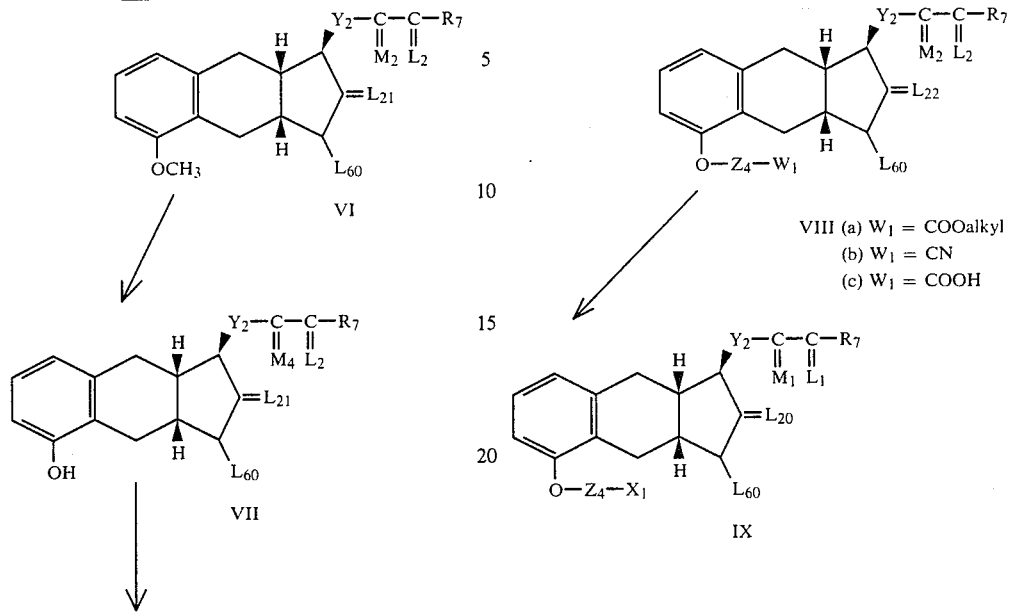

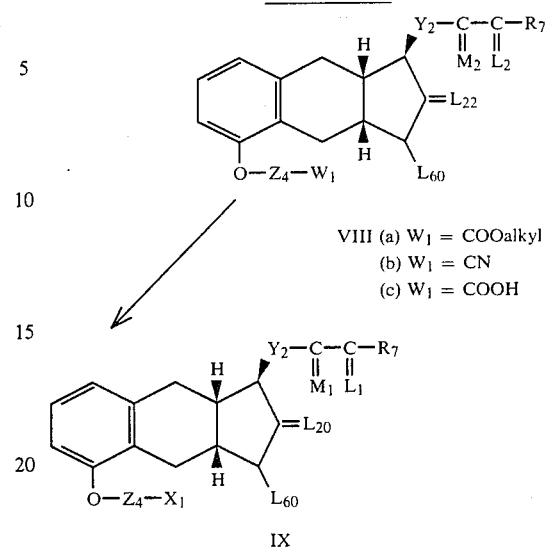

VIII (a) $W_1$ = COOalkyl
(b) $W_1$ = CN
(c) $W_1$ = COOH

CHART B

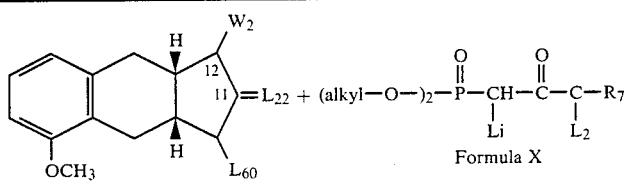

| Formula | $W_2$ | Formula | $W_2$ |
|---|---|---|---|
| XI | CHO | | |
| XII | trans-CH=CH—C(=O)—C(=$L_2$)—$R_7$ | XII(a) | trans-CH=CH—C(=O)—C(=$L_2$)—Rb |
| XIII | trans-CH=CH—C(=$M_3$)—C(=$L_2$)—$R_7$ | XIII(a) | trans-CH=CH—C(=$M_3$)—C(=$L_2$)—Rb |
| XIV | —CH$_2$CH$_2$—C(=$M_3$)—C(=$L_2$)—Ra | XIV(a) | —CH$_2$CH$_2$—C(=$M_3$)—C(=$L_2$)—Rb |
| XV | —CH$_2$CH$_2$—C(=$M_3$)—C(=$L_2$)—Rc | | |
| XVI | —C≡C—C(=$M_3$)—C(=$L_2$)—$R_7$ | XVI(a) | —C≡C—C(=$M_3$)—C(=$L_2$)—Rd |
| XVII | -cis-CH=CH—C(=$M_3$)—C(=$L_2$)—$R_7$ | XVII(a) | -cis-CH=CH—C(=$M_3$)—C(=$L_2$)—Rd |
| XVIII | -cis-CH=CH—C(=O)—C(=$L_2$)—$R_7$ | | |

CHART B-continued
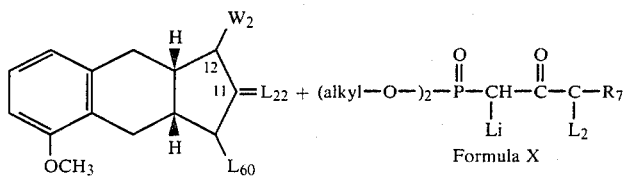
| Formula W₂ | Formula W₂ |
| --- | --- |
| 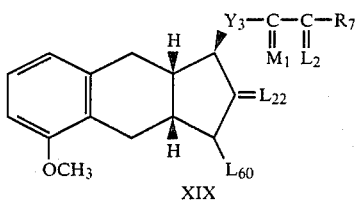 | |
CHART C
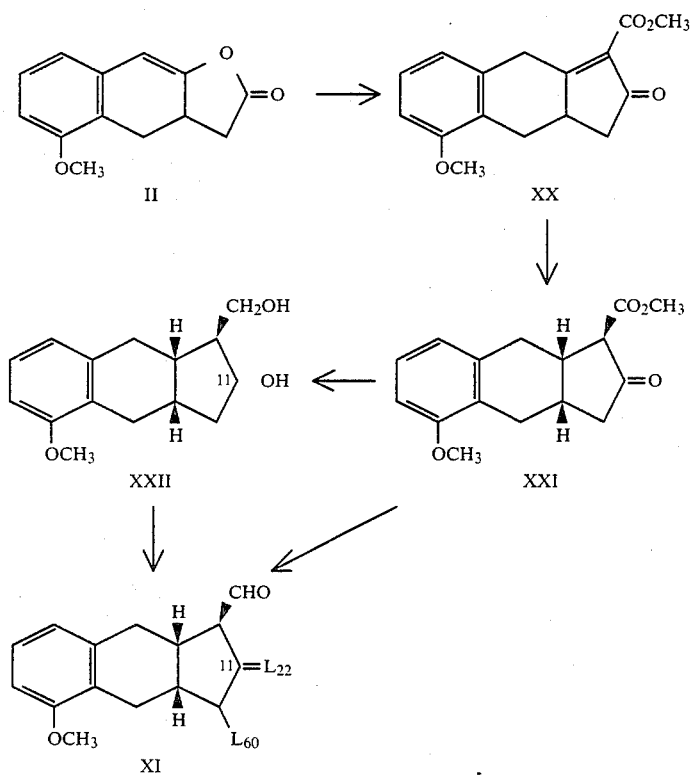
CHART D
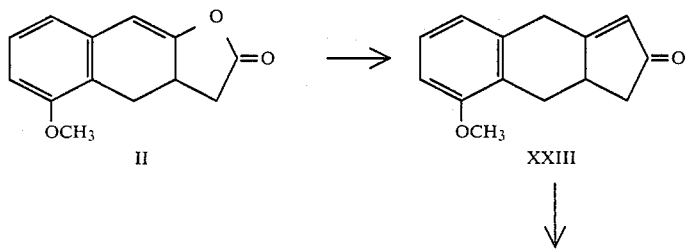

CHART D
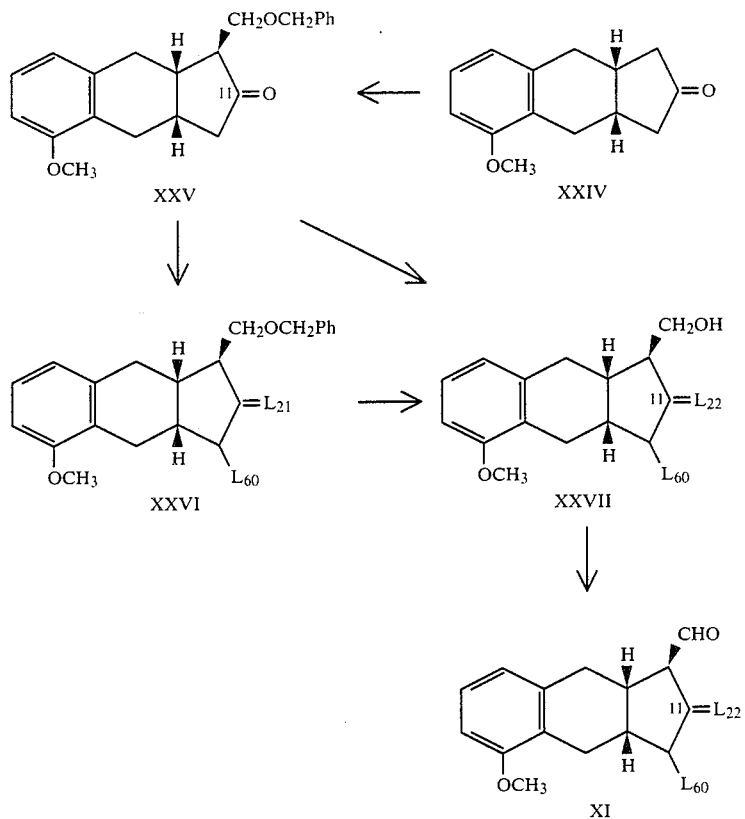
CHART E
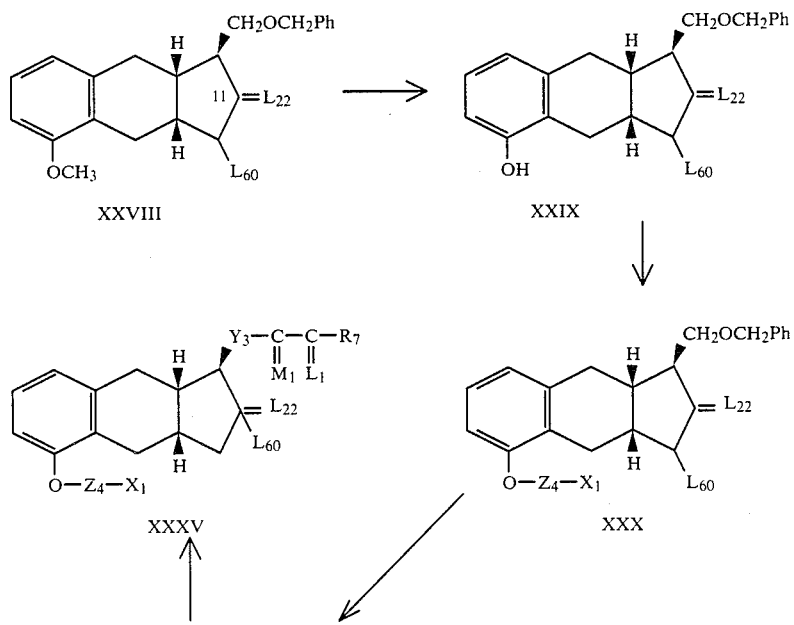

-continued
CHART E
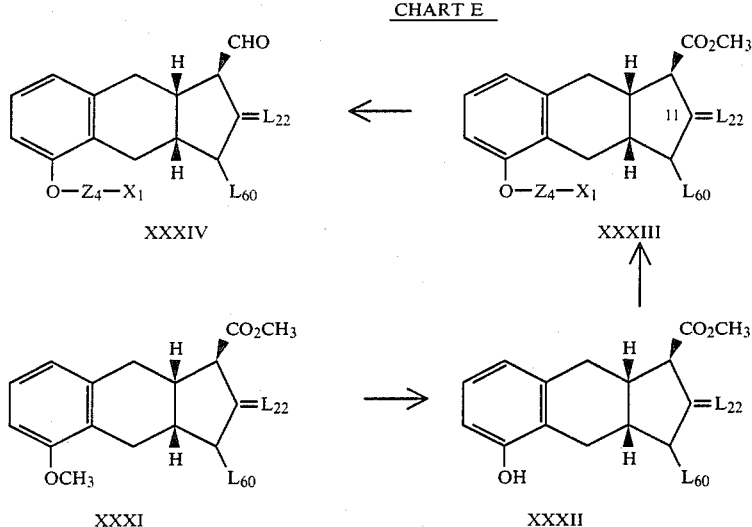
CHART F
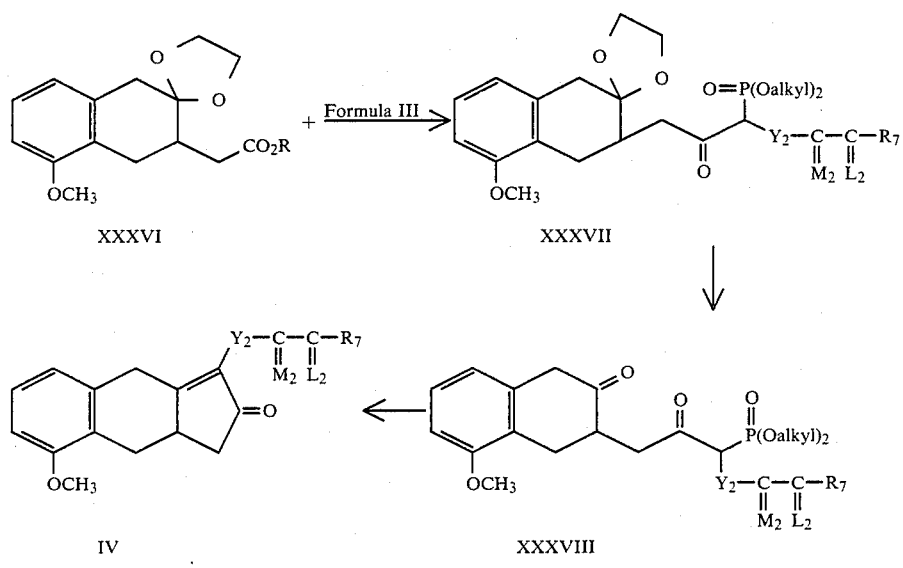
CHART G
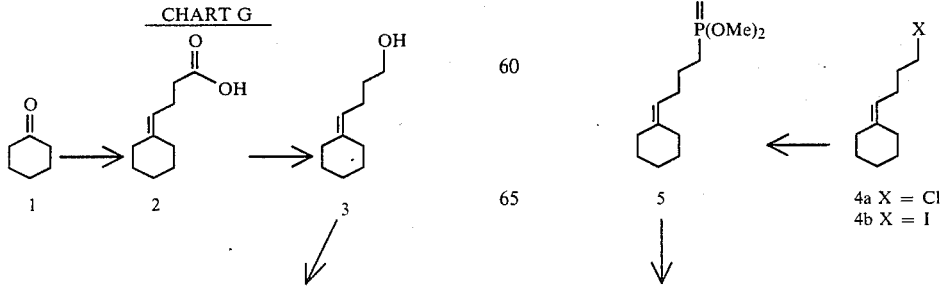

-continued
CHART G

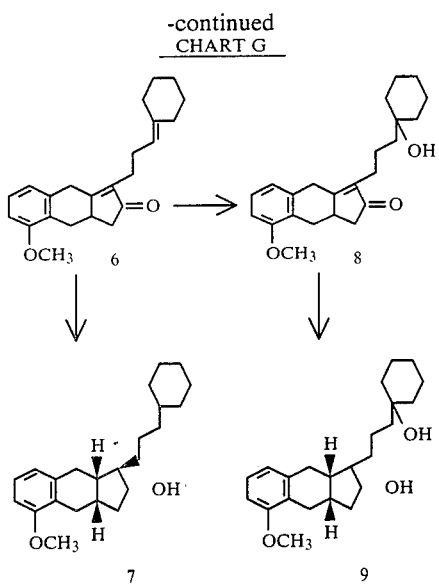

CHART H

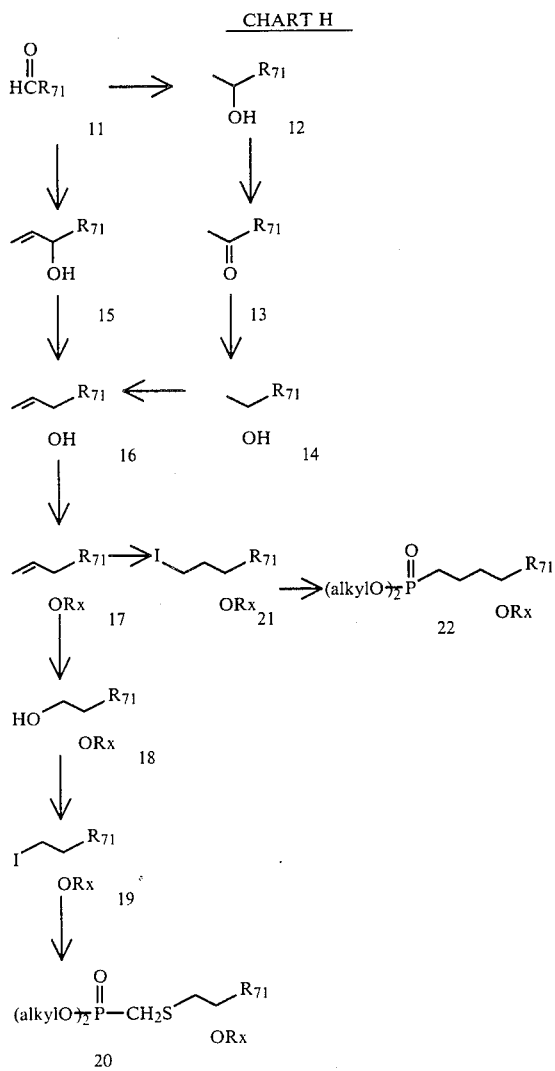

I claim:
1. A compound of the formula:

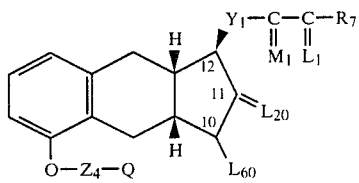

wherein Q is
(1) —COOR$_1$, wherein R$_1$ is
  (a) hydrogen;
  (b) (C$_1$-C$_{12}$) alkyl;
  (c) (C$_3$-C$_{10}$) cycloalkyl;
  (d) (C$_7$-C$_{13}$) aralkyl;
  (e) phenyl, optionally substituted with one, 2 or 3 chloro or (C$_1$-C$_3$) alkyl;
  (f) phenyl substituted in the para position by
    (i) —NHCOR$_{25}$,
    (ii) —COR$_{26}$,
    (iii)

$$-OCR_{54},$$

or
    (iv) —CH=N—NHCONH$_2$ wherein R$_{25}$ is methyl, phenyl, acetamidophenyl, benzamidophenyl, or —NH$_2$; R$_{26}$ is methyl, phenyl, —NH$_2$, or methoxy; R$_{54}$ is phenyl or acetamidophenyl; inclusive; or
  (g) a pharmacologically acceptable cation;
(2) —CH$_2$OH;
(3) —COL$_4$, wherein L$_4$ is
  (a) amino of the formula —NR$_{51}$R$_{52}$ wherein R$_{51}$ and R$_{52}$ are
    (i) hydrogen,
    (ii) (C$_1$-C$_{12}$) alkyl,
    (iii) (C$_3$-C$_{10}$) cycloalkyl,
    (iv) (C$_7$-C$_{12}$) aralkyl,
    (v) phenyl, optionally substituted with one 2 or 3 chloro, (C$_1$-C$_3$) alkyl, hydroxy, carboxy, (C$_2$-C$_5$) alkoxycarbonyl, or nitro,
    (vi) (C$_2$-C$_5$) cyanoalkyl,
    (vii) (C$_2$-C$_5$) carboxyalkyl,
    (viii) (C$_2$-C$_5$) carbamoylalkyl,
    (ix) (C$_3$-C$_6$) acetylalkyl,
    (x) (C$_7$-C$_{11}$) benzoalkyl, optionally substituted by one, 2 or 3 chloro, (C$_1$-C$_3$) alkyl, hydroxy, (C$_1$-C$_3$) alkoxy, carboxy, (C$_2$-C$_5$) alkoxy carbonyl, or nitro,
    (xi) pyridyl, optionally substituted by one, 2 or 3 chloro, (C$_1$-C$_3$) alkyl, or (C$_1$-C$_3$) alkoxy,
    (xii) (C$_6$-C$_9$) pyridylalkyl optionally substituted by one, 2 or 3 chloro, (C$_1$-C$_3$) alkyl, hydroxy, or (C$_1$-C$_3$) alkoxy,
    (xiii) (C$_1$-C$_4$) hydroxyalkyl,
    (xiv) (C$_1$-C$_4$) dihydroxyalkyl,
    (xv) (C$_1$-C$_4$) trihydroxyalkyl, with the proviso that not more than one of R$_{51}$ and R$_{52}$ is other than hydrogen or alkyl;
  (b) cycloamino selected from the group consisting of pyrolidino, piperidino, morpholino, piperazino, hexamethylenimino, pyrrolino, or 3,4-didehydropiperidinyl optionally substituted by one or 2 (C$_1$-C$_{12}$) alkyl of one to 12 carbon atoms, inclusive;

(c) carbonylamino of the formula —NR$_{53}$COR$_{51}$ wherein R$_{53}$ is hydrogen or (C$_1$-C$_4$) alkyl and R$_{51}$ is other than hydrogen, but otherwise defined as above;

(d) sulfonylamino of the formula —NR$_{53}$SO$_2$R$_{51}$, wherein R$_{51}$ and R$_{53}$ are defined in (c);

(4) —CH$_2$NL$_2$L$_3$ wherein L$_2$ and L$_3$ are hydrogen or (C$_1$-C$_4$) alkyl, being the same or different, or the pharmacologically acceptable acid addition salts thereof when X$_1$ is —CH$_2$NL$_2$L$_3$;

(5) —CN;

wherein Z$_4$ is —CH$_2$—, —CH$_2$CH$_2$—, —CF$_2$—, or —CH$_2$CF$_2$;

wherein L$_{20}$ is α-OH,β-H; α-H,β-OH, H,H; α-CH$_3$, β-H; α-CH$_2$OH,β-H; =O; or =CH$_2$; wherein L$_{60}$ is hydrogen or L$_{20}$ and L$_{60}$ taken together form a double bond between positions 10 and 11;

wherein Y$_1$ is —CH$_2$CH$_2$—, —SCH$_2$—, —C≡C—, trans —CH=CH—, or cis —CH=CH—;

wherein

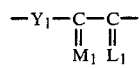

taken together is

wherein M$_1$ is α-H:β-H; =O; α-OH:β-R$_5$; or α-R$_5$:β-OH; wherein R$_5$ is hydrogen or methyl;

wherein L$_1$ is (1) α-R$_3$:β-R$_4$, α-R$_4$:β-R$_3$, or mixtures thereof wherein R$_3$ and R$_4$ are hydrogen, methyl, or fluoro, being the same or different, with the proviso that one of R$_3$ and R$_4$ is fluoro only when the other is hydrogen or fluoro;

(2) or when M$_1$ is α-H:β-H L$_1$ is α-OH:β-R$_3$, α-R$_3$:β-OH; or a mixture of α-OH:β-R$_3$ and α-R$_3$:β-OH wherein R$_3$ is hydrogen, methyl, vinyl, or ethynyl;

wherein R$_7$ is —(CH$_2$)$_m$—OCH$_3$, wherein m is an integer from 2 to 5, inclusive and said group is straight or branched; or wherein

taken together is (1)

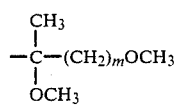

wherein m is an integer of from 2 to 5 inclusive;

(2)

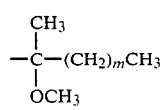

wherein m is an integer of from 2 to 5 inclusive;

(3)

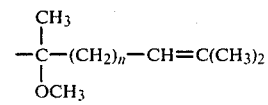

wherein n is an integer of from 1 to 4 inclusive; or (4)

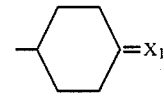

wherein X$_1$ is =O; F,F; α-H,β-OH and α-OH,β-H;

(5)

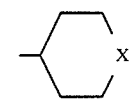

wherein X is —O—, —S—, or —NH;

(6)

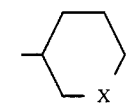

wherein X is as defined above;

(7)

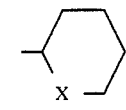

wherein X is as defined above;

(8) phenyl optionally substituted with one, 2 or 3 chloro, fluoro, trifluoromethyl, C$_1$-C$_3$ alkyl, or C$_1$-C$_3$ alkoxy with the proviso that not more than two substituents are other than alkyl;

wherein

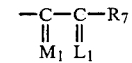

taken together is (1)

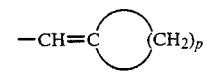

wherein p is an integer of from 3 to 7 inclusive;

(2)

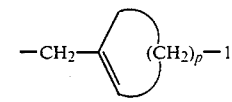

wherein p is as defined above;

(3)

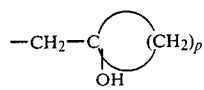

wherein p is as defined above; and the (4) benzyl optionally substituted on the aromatic ring with one, 2 or 3 chloro, fluoro, trifluoromethyl, $C_1$-$C_3$ alkyl, or $C_1$-$C_3$ alkoxy with the proviso that not more than two substituents are other than alkyl; individual optical enantiomers and salts thereof.

2. A compound of claim 1 wherein $M_1$ is $\alpha$-H,$\beta$-OH; $\alpha$-OH,$\beta$-H, or H,H.

3. A compound of claim 2 wherein $L_{20}$ is $\alpha$-$CH_3$,$\beta$-H or $\alpha$-OH,$\beta$-H.

4. A compound of claim 3 wherein $Z_4$ is —$CH_2$—.

5. A compound of claim 3 wherein $X_1$ is $COOR_1$.

6. A compound of claim 5 wherein $R_1$ is hydrogen, or ($C_1$-$C_{12}$) alkyl or a pharmaceutically acceptable cation.

7. A compound of claim 3 wherein —$C(L_1)R_7$ is

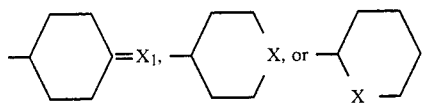

8. A compound of claim 7 wherein X or $X_1$ is oxygen.

9. A compound of claim 7 wherein $X_1$ is F,F or H,OH.

10. A compound of claim 3 wherein —$C(M_1)C(L_1)R_7$ is

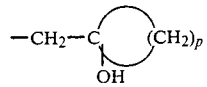

or benzyl optionally substituted on the aromatic ring with one, 2, or 3 chloro, fluoro, trifluoromethyl, $C_1$-$C_3$ alkyl or $C_1$-$C_3$ alkoxy with the proviso that not more than two substituents are other than alkyl.

11. A compound of claim 10 wherein p is 5.

12. A compound of claim 10 which is 15-cyclohexyl-9,15-dideoxy-13,14-dihydro-2',9$\alpha$-methano-3-oxa-4,5,6,16,17,18,19,20-octanor-3,7-(1',3'-interphenylene)-$PGF_1$ and salts and optical isomers thereof.

13. A compound of claim 10 which is 15-cyclohexyl-9,15-dideoxy-13,14-dihydro-16(RS)hydroxy-2',9$\alpha$-methano-3-oxa-4,5,6,16,17,18,19,20-octanor-3,7-(1',3'-interphenylene)-$PGF_1$ and salts and optical isomers thereof.

14. A compound of claim 10 which is 15-phenyl-9,15-dideoxy-13,14-dihydro-2',9$\alpha$-methano-3-oxa-4,5,6,16,17,18,19,20-octanor-3,7-(1',3'-interphenylene)-$PFG_1$ and salts and optical isomers thereof.

15. A compound of formula I(a), formula I(b), formula I(c), or formula I(d) having the following structures:

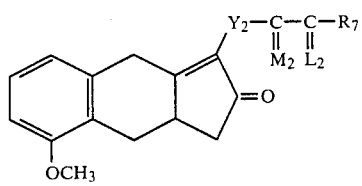

Formula I(a)

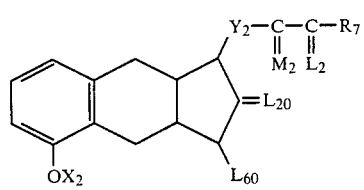

Formula I(b)

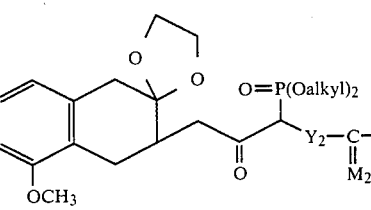

Formula I(c)

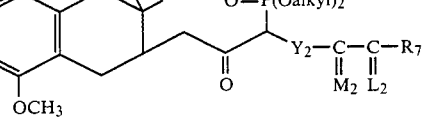

Formula I(d)

wherein the symbols $Y_2$, $M_1$, $L_1$, $L_{20}$, $L_{60}$, $X_2$, and $R_7$, have the meanings set forth in claim 1 and wherein alkyl has from 1 to 4 carbon atoms.

* * * * *